US011266502B1

(12) United States Patent
Wallace et al.

(10) Patent No.: US 11,266,502 B1
(45) Date of Patent: Mar. 8, 2022

(54) SYSTEM AND METHOD FOR CARDIAC VALVE REPAIR

(71) Applicant: Versa Vascular Inc., Oakland, CA (US)

(72) Inventors: Daniel T. Wallace, Santa Cruz, CA (US); Juan Granada, Upper Saddle River, NJ (US); Jeremy J. Boyette, Woodside, CA (US); Peter W. Gregg, Santa Cruz, CA (US); Spencer C. Noe, San Miguel, CA (US); Evelyn N. Haynes, Los Gatos, CA (US)

(73) Assignee: Versa Vascular Inc., Oakland, CA (US)

( * ) Notice: Subject to any disclaimer, the term of this patent is extended or adjusted under 35 U.S.C. 154(b) by 0 days.

(21) Appl. No.: 17/227,847

(22) Filed: Apr. 12, 2021

Related U.S. Application Data

(60) Provisional application No. 63/125,035, filed on Dec. 14, 2020.

(51) Int. Cl.
*A61F 2/24* (2006.01)

(52) U.S. Cl.
CPC ............ *A61F 2/2442* (2013.01); *A61F 2/246* (2013.01); *A61F 2/2445* (2013.01); *A61F 2/2463* (2013.01); *A61F 2/2466* (2013.01); *A61F 2220/0016* (2013.01)

(58) Field of Classification Search
CPC ...... A61F 2/2442; A61F 2/246; A61F 2/2463; A61F 2/2466; A61F 2/2445
See application file for complete search history.

(56) References Cited

U.S. PATENT DOCUMENTS

| | | | |
|---|---|---|---|
| 6,540,782 B1 * | 4/2003 | Snyders | A61F 2/2436 623/2.14 |
| 7,785,366 B2 | 8/2010 | Maurer et al. | |
| 8,070,805 B2 | 12/2011 | Vidlund et al. | |
| 8,486,136 B2 | 7/2013 | Maurer et al. | |
| 9,636,223 B2 | 5/2017 | Khalil et al. | |
| 9,814,576 B2 | 11/2017 | Yellin et al. | |
| 10,195,021 B2 | 2/2019 | Keranen et al. | |
| 10,238,491 B2 | 3/2019 | Tobis et al. | |
| 10,285,812 B2 | 5/2019 | Rowe et al. | |
| 10,548,727 B2 | 2/2020 | Khalil et al. | |
| 10,595,994 B1 | 3/2020 | Christianson et al. | |
| 10,765,518 B2 | 9/2020 | Pesce et al. | |

(Continued)

*Primary Examiner* — William H Matthews
(74) *Attorney, Agent, or Firm* — Polsinelli PC

(57) ABSTRACT

A cardiac valve repair implant, wherein the implant includes a central occluder, and frame and a thin sheet. The central occluder includes a central longitudinal axis. The frame extends proximally from the central occluder and is centered about and forms a circumference around the central longitudinal axis of the central occluder. The frame self-biases from a collapsed state to an expanded state. A proximal end of the frame projects proximally when the frame is in the collapsed state. The proximal end of the frame projects radially outward away from the central longitudinal axis of the central occluder when the frame is in the expanded state. The thin sheet is supported on a proximal portion of the frame. When the frame is in the expanded state, the thin sheet forms an annular surface defining an inner circular opening centered about the central longitudinal axis of the central occluder.

21 Claims, 25 Drawing Sheets

(56) References Cited

U.S. PATENT DOCUMENTS

| | | | |
|---|---|---|---|
| 2012/0323317 A1* | 12/2012 | Karapetian | ............ A61F 2/2409 623/2.37 |
| 2017/0172737 A1 | 6/2017 | Kuetting et al. | |
| 2018/0168803 A1 | 6/2018 | Pesce et al. | |
| 2019/0060072 A1 | 2/2019 | Zeng | |
| 2019/0201191 A1 | 7/2019 | McLean et al. | |
| 2019/0388218 A1 | 12/2019 | Vidlund et al. | |
| 2020/0078167 A1 | 3/2020 | Quijano et al. | |
| 2020/0113679 A1 | 4/2020 | Pesce et al. | |
| 2020/0121458 A1 | 4/2020 | Vidlund et al. | |

* cited by examiner

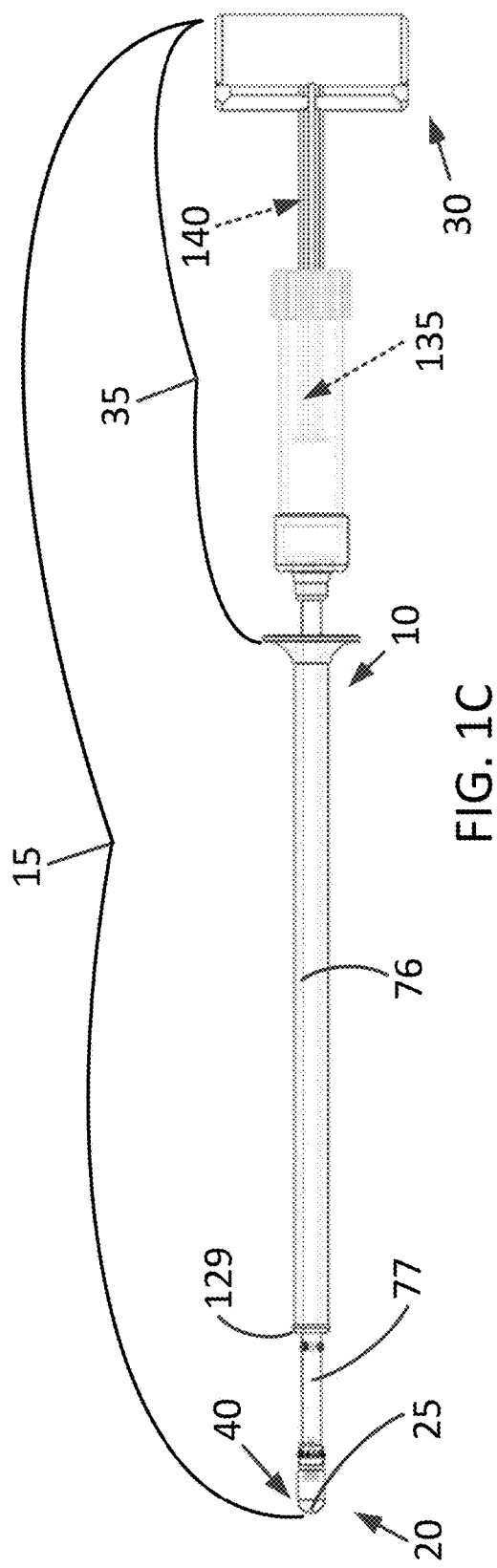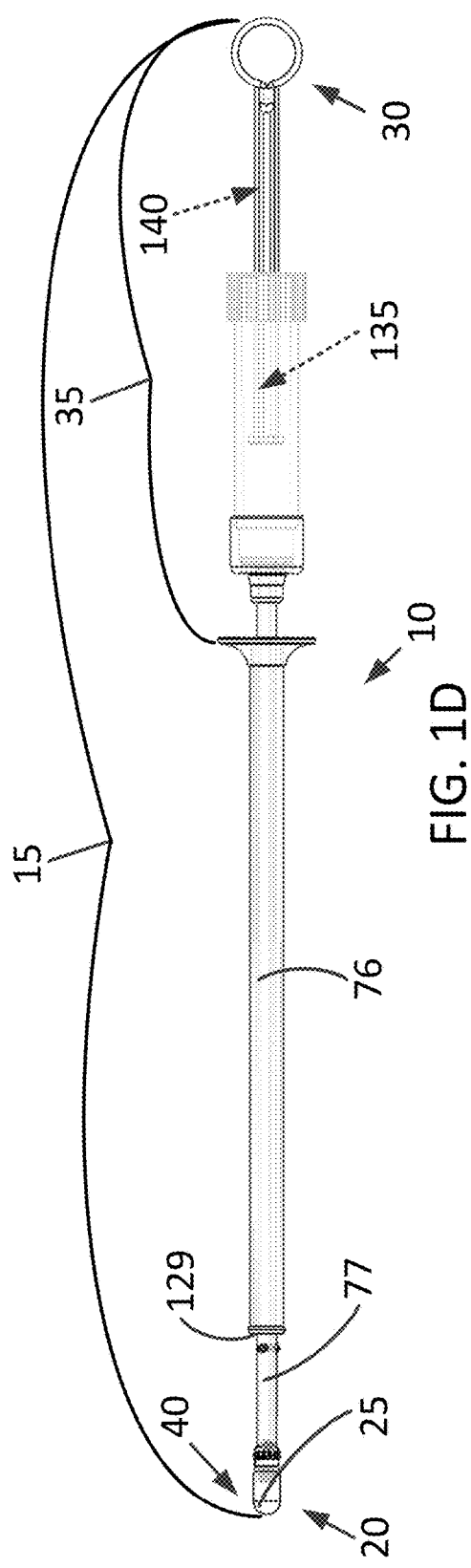

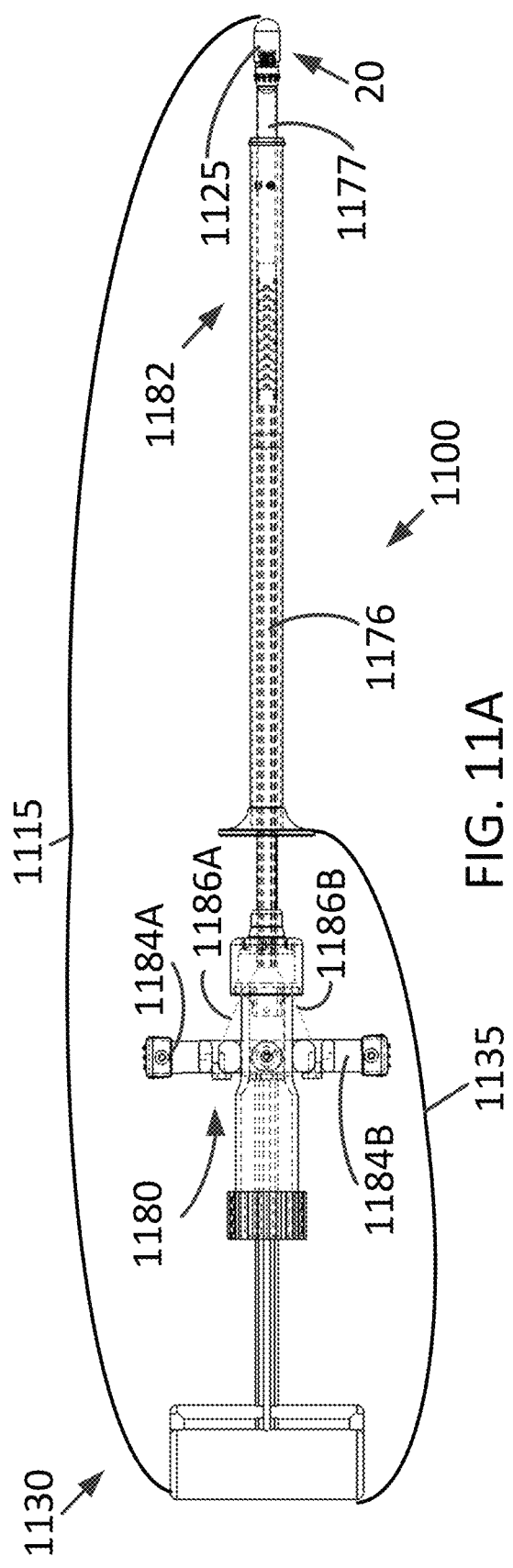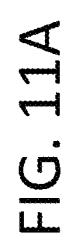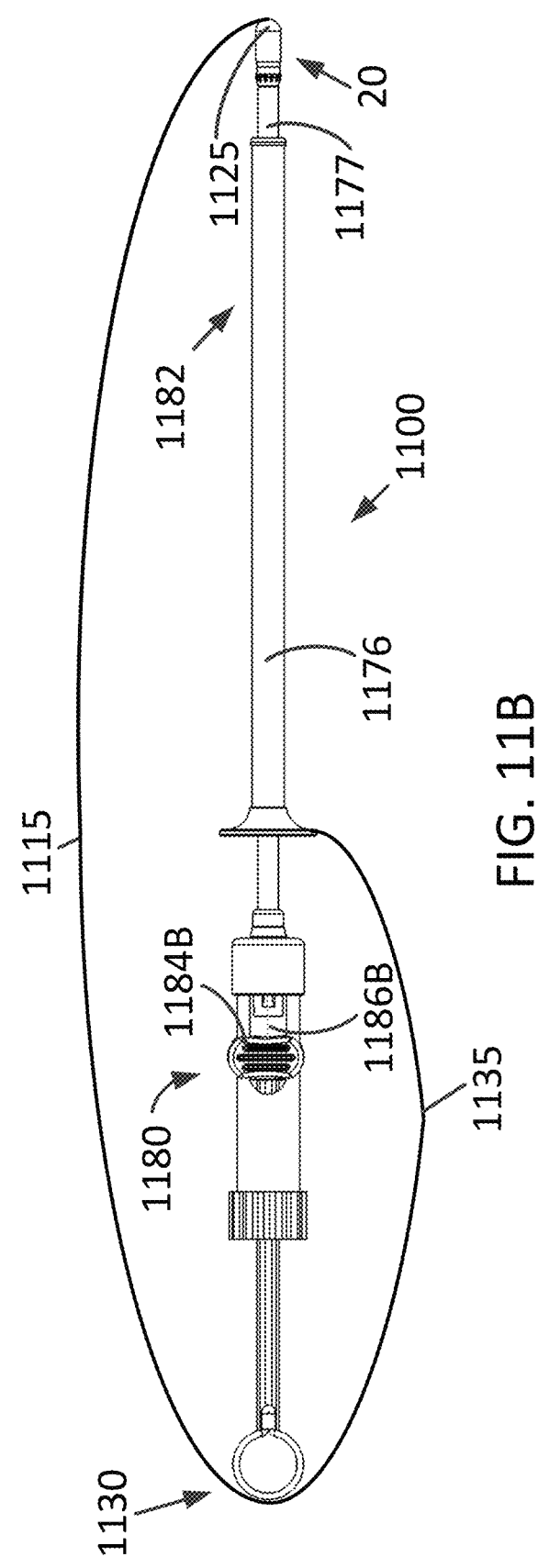
FIG. 11A
FIG. 11B

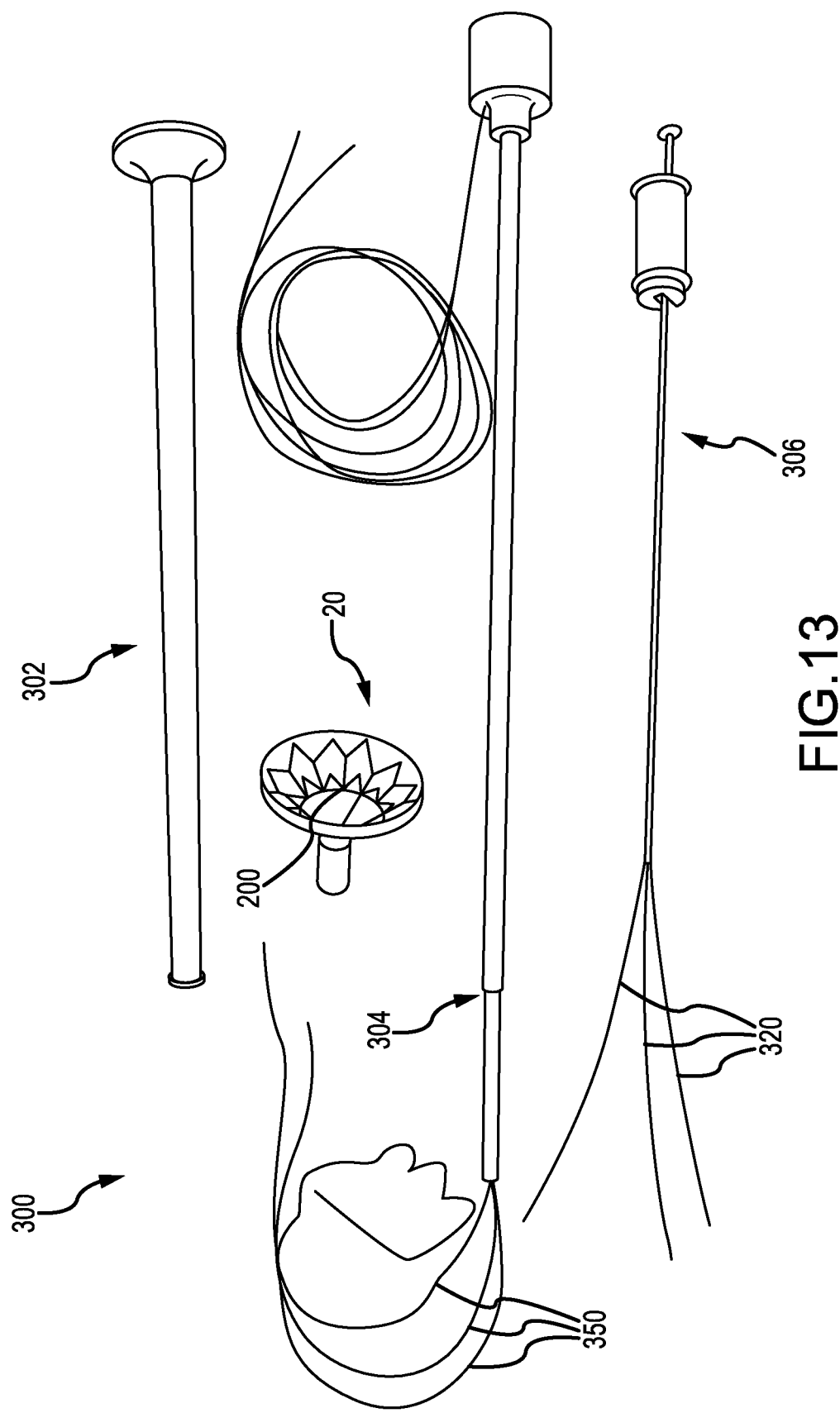

SYSTEM AND METHOD FOR CARDIAC VALVE REPAIR

CROSS-REFERENCE TO RELATED APPLICATIONS

This application is related to and claims priority under 35 U.S.C. § 119(e) from U.S. Patent Application No. 63/125,035, filed Dec. 14, 2020, and titled "System and Method for Cardiac Valve Repair", the entire contents of which are incorporated herein by reference for all purposes.

TECHNICAL FIELD

The present disclosure relates to medical systems and methods for repairing a cardiac valve. More specifically, the present disclosure pertains to a cardiac valve repair implant that is minimally invasively deliverable and implantable via an associated minimally invasive delivery tool.

BACKGROUND

Cardiac valve regurgitation occurs when a cardiac valve does not close completely, causing blood to leak back through the valve. The causes of regurgitation may vary. Functional regurgitation is caused by changes to the heart geometry near the valve, where, for example, the heart enlarges, inducing both geometrical distortion around the valve annulus and insufficient leaflet coaptation during valve closure.

Degenerative regurgitation is caused by a disease of the valve itself, where, for example, the leaflets may thicken and be unable to seal completely. In both cases, the patient suffers because high-pressure blood in the ventricle regurgitates through the valve into the low-pressure venous system.

Surgical repair and replacement may successfully treat tricuspid and mitral regurgitation, but surgery is costly and traumatic. Specifically, the surgical treatments require general anesthesia, a stopped heart with extracorporeal bypass, and either valve replacement or repair. The surgical treatments require painful recovery over a period of approximately three weeks. As a result, surgical treatment is often not performed because cost, recovery time, pain, and, for older patients, mortality risk may be prohibitive.

Cardiac valves may also be repaired via percutaneous systems and methods. For example, a percutaneous treatment may navigate a Nitinol clip between the valve leaflets to permanently clip the leaflets together. The percutaneous clip procedure results in a relatively pain-free recovery within days, and this procedure has successfully treated hundreds of thousands mitral regurgitation patients. Unfortunately, the percutaneous clip procedure is costly and difficult to perform, particularly by inexperienced operators. Further, the feasibility of the percutaneous clip procedure for the tricuspid valve is unproven and may be less effective in a three-leaflet valve. In addition, the mechanisms of valvular regurgitation are multiple and fixing a single mechanism of disease (e.g., leaflet grasping) may temporarily reduce the severity of regurgitation but not improve the natural history of the disease (e.g., deterioration over time).

Accordingly, there is a need for a system for repairing a cardiac valve that is simple to deliver, targets several disease components simultaneously, and improves overall results as compared to conventional treatments. There is also a need for a method of making such a repair.

BRIEF SUMMARY

Aspects of the present disclosure may include a cardiac valve repair implant. In one embodiment, the implant includes a central occluder, and frame and a thin sheet. The central occluder includes a central longitudinal axis. The frame extends proximally from the central occluder and is centered about and forms a circumference around the central longitudinal axis of the central occluder. The frame self-biases from a collapsed state to an expanded state. A proximal end of the frame projects proximally when the frame is in the collapsed state. The proximal end of the frame projects radially outward away from the central longitudinal axis of the central occluder when the frame is in the expanded state. The thin sheet is supported on a proximal portion of the frame. When the frame is in the expanded state, the thin sheet forms an annular surface defining an inner circular opening centered about the central longitudinal axis of the central occluder.

The frame may include anchor members on a distal side of the frame, the anchor members protruding distally from the frame when the frame is in the expanded state. The anchor members may additionally protrude radially outward when the frame is in the expanded state. Alternatively, the anchor members may additionally protrude radially inward when the frame is in the expanded state.

The frame may include spokes that extend between a proximal end of the central occluder and the proximal portion of the frame that supports the thin sheet. The spokes may be substantially straight and parallel to the central longitudinal axis of the central occluder when the frame is in the collapsed state, and the spokes may curve radially outward relative to the central longitudinal axis of the central occluder when the frame is in the expanded state.

The proximal portion of the frame that supports the thin sheet may include arcuate petal portions extending from the spokes. Each arcuate petal portion may include an outer arcuate member and an inner arcuate member radially inward of the outer arcuate member.

The thin sheet may be supported on a distal side of the frame. Alternatively or additionally, the thin sheet may be supported on a proximal side of the frame.

The central occluder may include a cylindrical side surface and a bullnose extending distally from the cylindrical side surface. The frame may include a shape-memory material that self-biases the frame from the collapsed state to the expanded state. The thin sheet may include a fabric material that allows for tissue ingrowth.

Aspects of the present disclosure may also include a method of repairing a target cardiac valve. In one embodiment, the method includes: delivering an implant in a collapsed state into an atrium adjacent the target cardiac valve, the implant including a central occluder with a central longitudinal axis, a frame extending proximally from the central occluder, and a thin sheet supported on a proximal region of the frame, wherein when the implant is in the collapsed state, the frame and thin sheet are folded inward about the central longitudinal axis; approaching the target cardiac valve with the implant in an expanded state, wherein when the implant is in the expanded state, the frame and thin sheet are unfolded and form an annular structure defining an inner circular opening centered about the central longitudinal axis of the central occluder; and positioning the central occluder in an orifice of the target cardiac valve and a distal side of the annular structure against an annular region of cardiac tissue surrounding the target cardiac valve such that the inner circular opening opens over the orifice of the target cardiac valve.

The implant may be delivered to the target valve via an antegrade percutaneous route. The implant may self-bias from the collapsed state to the expanded state.

A proximal end of the frame may project proximally when the frame is in the collapsed state. The proximal end of the frame may project radially outward away from the central longitudinal axis of the occluder when the frame is in the expanded state.

The frame may include anchor members on a distal side of the annular structure. The anchor members may protrude into the annular region of cardiac tissue surrounding the target cardiac valve. The implant may be over expanded to cause the anchor members to protrude into the annular region. The implant may be pushed distally against the annular region of cardiac tissue surrounding the target cardiac valve to cause the anchor members to protrude into the annular region.

The frame may include spokes that extend between a proximal end of the central occluder and the proximal portion of the frame that supports the thin sheet. The frame may include a shape-memory material that self-biases the implant from the collapsed state to the expanded state. The thin sheet may include a fabric material that allows for tissue ingrowth.

The central occluder may be positioned in the orifice of the target cardiac valve such that the leaflets of the target cardiac valve abut against a cylindrical side of the central occluder.

BRIEF DESCRIPTION OF THE DRAWINGS

FIG. 1C is a plan view of the valve repair system of FIG. 1A.

FIG. 1D is a side elevation view of the valve repair system of FIG. 1A.

FIGS. 11A-11C are illustrations of a system for repairing a cardiac valve and, more specifically, a plan view, side elevation view, and a plan view illustrating a range of motion of a delivery tool of the system, respectively.

FIG. 13 is an illustration of an example implantable cardiac valve repair system in a disassembled configuration and including each of an implant and a delivery tool.

DETAILED DESCRIPTION

Figure 1A:
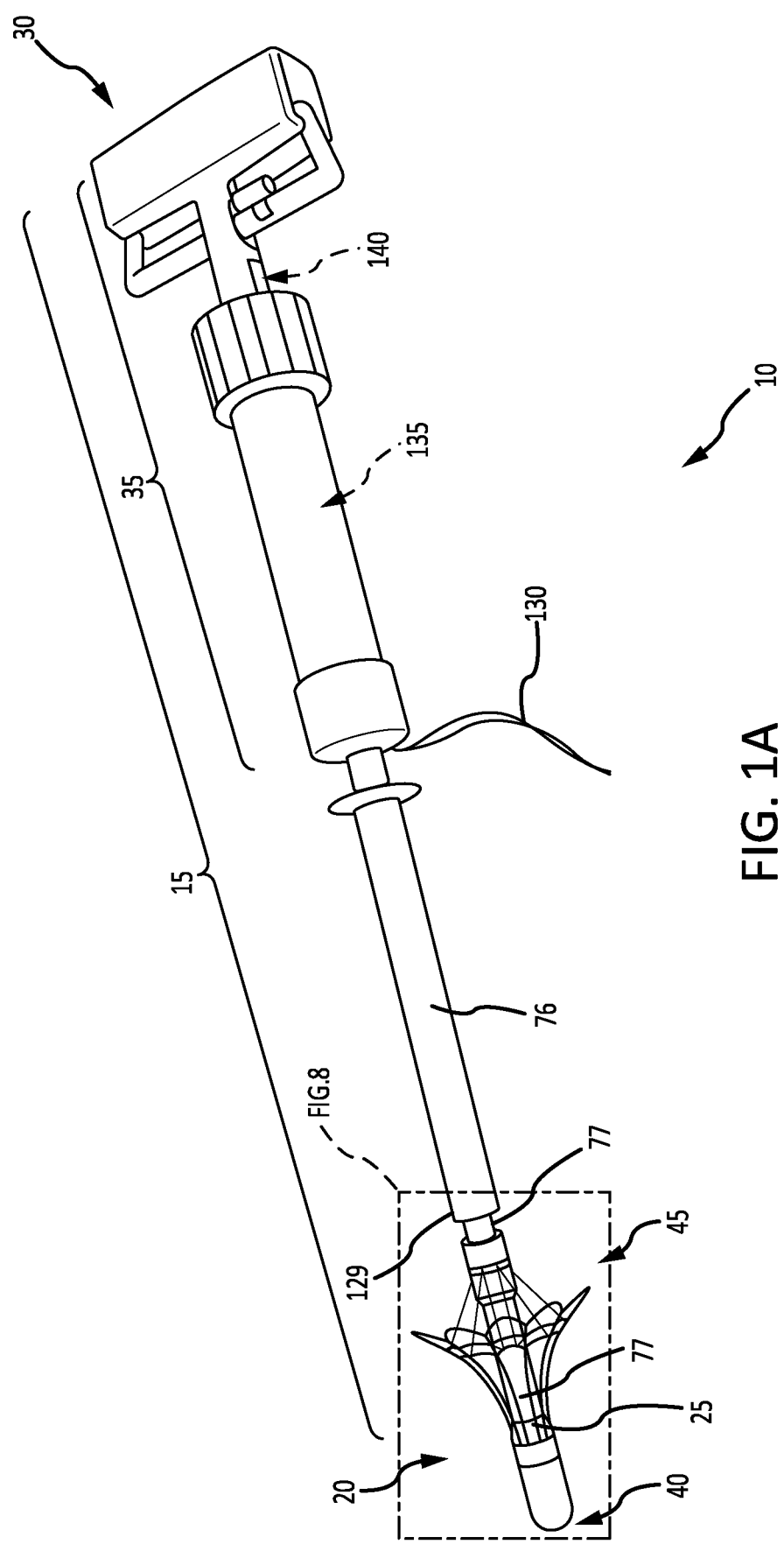
FIG. 1A is an illustration of a system for repairing a cardiac valve, the system including a minimally invasive delivery tool and an implantable cardiac valve repair implant supported on a distal end of the delivery tool and that is deliverable and implantable via the delivery tool.
Figure 1B:
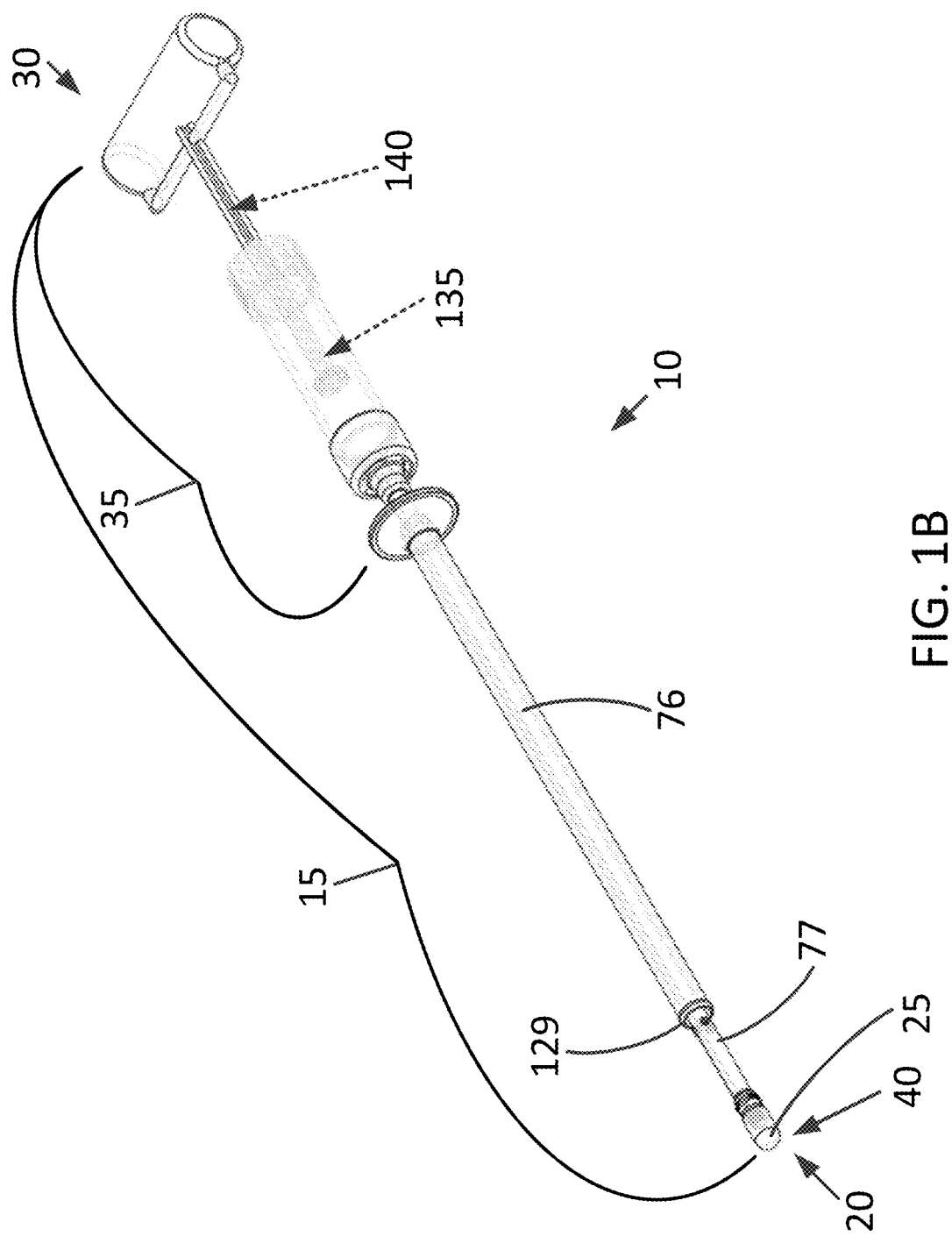
FIG. 1B is an isometric view of the valve repair system of FIG. 1A.

For a brief overview of the cardiac valve repair system 10 disclosed herein, reference is made to FIGS. 1A-1D. In particular, FIG. 1A is an illustration of the cardiac valve repair system 10 while FIGS. 1B-1D are isometric, plan, and side elevation views, respectively of the valve repair system 10. As can be understood from FIG. 1A, the system 10 includes a delivery and deployment tool 15 and an implantable cardiac valve repair device or implant 20 supported on a distal end 25 of the tool 15. The tool 15 includes a proximal end 30 opposite the tool distal end 25. The tool proximal end 30 includes a control handle 35 used by a physician to manipulate the tool 15 in positioning the implant 20 at the target site and deploying the implant 20 within the target site, which is a cardiac valve in need of repair, as discussed in detail later in this Detailed Description. In one embodiment, the tool 15 is used for minimally invasive delivery and deployment of the implant 20 in the cardiac valve in need of repair.

The system and its implant are advantageous in that the implant may be delivered and deployed at the target site via an antegrade percutaneous route (e.g., a trans-femoral or trans-jugular route) with the patient consciously sedated during the procedure. It is anticipated the implantation stage may take less than 60 minutes, and the implant and delivery system will have a cost substantially less expensive than prior cardiac valve repair systems. Finally, the regurgitation grade afforded by a cardiac valve repair completed via the implant 20 disclosed herein will be 2+ or lower. Accordingly, the cardiac repair system 10 is a significant improvement over prior art systems as it is atraumatic, materially less expensive and less time intensive, all while providing a significant improvement in the reduction of regurgitation.

I. Cardiac Valve Repair Implant

To begin a detailed discussion of the cardiac valve repair implant 20, reference is made to FIGS. 2-6, which are various views of an embodiment of the implant 20 when the implant is in an expanded state that exists when the implant is implanted in the cardiac valve to be repaired. As illustrated in these figures, the implant includes a distal end 40 and a proximal end 45. The distal end 40 serves as the leading end of the implant 20 during implantation, as can be understood from FIG. 1A-1D.

As illustrated in FIGS. 2-6, the implant 20 further includes a central occluder 50, a frame 55 and a thin sheet 60 (also referred to herein as a thin layer 60) supported on the frame. The frame 55 extends proximally from a proximal end 65 of the central occluder 50. When in the expanded state, the frame 55 radiates laterally outwardly relative to a central longitudinal axis 70 (see FIG. 5) of the implant 20, and the thin sheet 60 forms an annular surface 62 supported on the expanded frame 55. The annular surface 62 has a distal radially inward edge 63 and a proximal radially outward edge 64. The distal radially inward edge 63 defines a central opening 66 in the thin sheet 60 and the implant 20. The proximal radially outward edge 64 forms the extreme proximal radially outward boundary of this embodiment of the implant when in the expanded state. The central longitudinal axis 70 passes through the extreme distal tip 75 of the central occluder 50 and a center point 80 (see FIG. 4) of the proximal end 65 of the central occluder. In light of the foregoing and in at least certain embodiments, the frame 55 is generally designed to sit on the floor of the atrium, to induce annular reduction, and to produce a neo-annulus.

Figure 10:
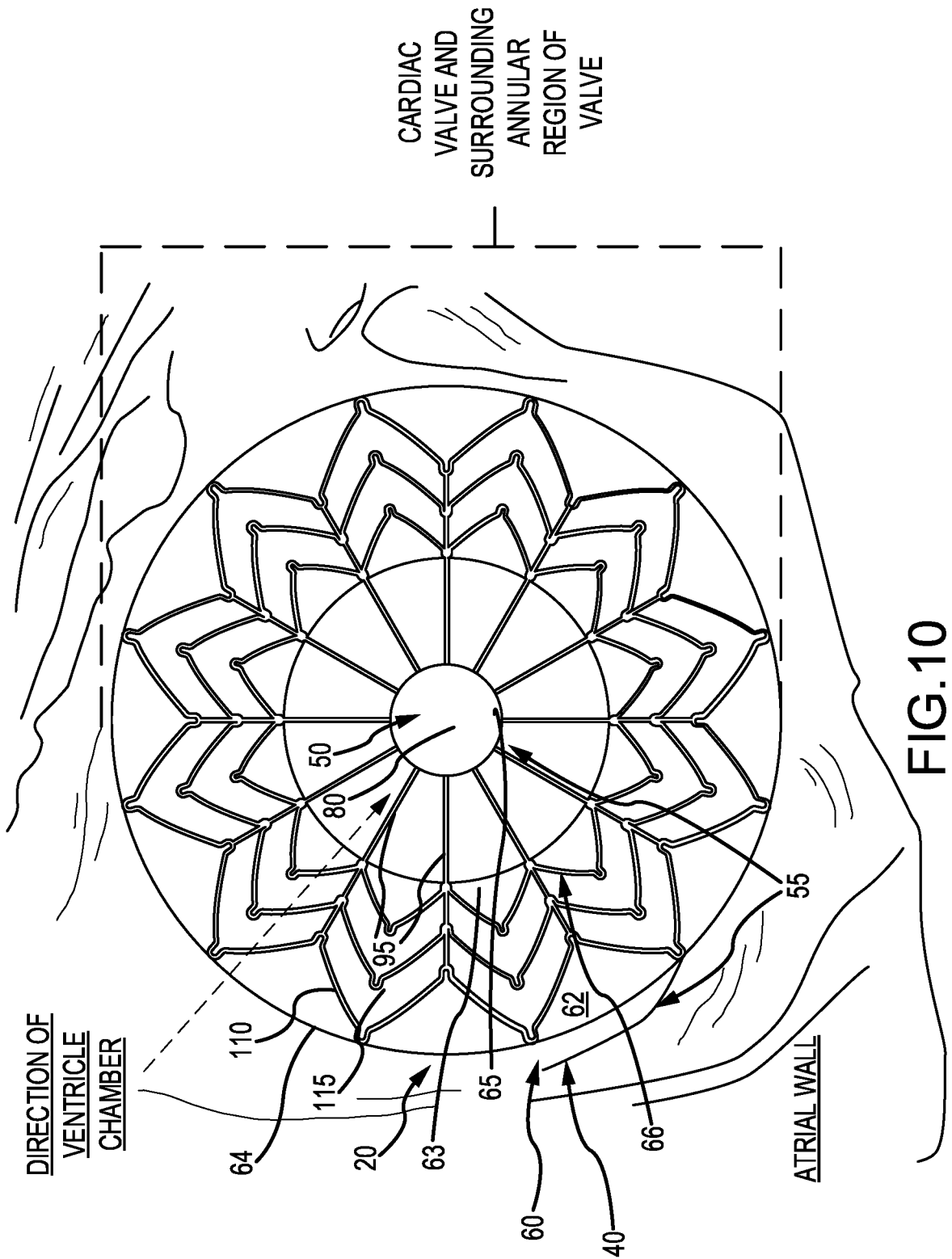
FIG. 10 is a view of the implantable cardiac valve repair implant implanted in a target cardiac valve, as viewed from an atrial position looking towards the valve and the ventricle chamber below.

As can be understood from FIGS. 2-6, in addition to being annular, the annular surface 62 may also be conical, or relatively so (e.g., parabolic), such that its proximal side, which faces the atrial chamber when the implant 20 is implanted in the target cardiac valve as depicted in FIG. 10, serves as a funnel arrangement distally leading from the atrial chamber towards the central opening 66 of the implant 20 and the valve opening distal the central opening 66. Similarly, the distal side of the annular surface 62 may also be conical to generally make mating surface contact with the semi-conical regions of the atrial wall surface and surrounding annular region of the target cardiac valve, as can be understood from FIG. 10.

Figure 6:
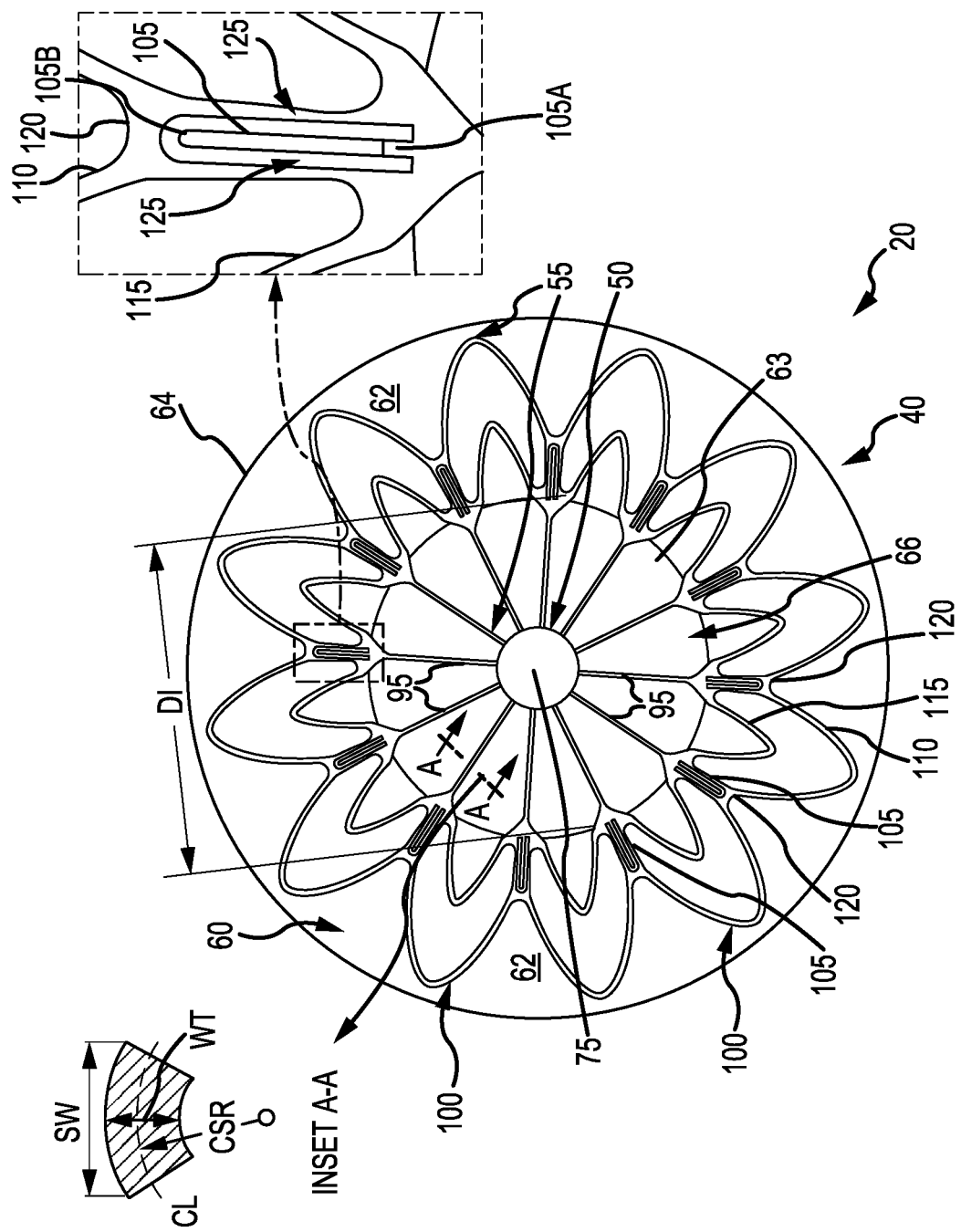
FIG. 6 is a distal plan view of the implantable cardiac valve repair implant in the expanded state.
Figure 7:
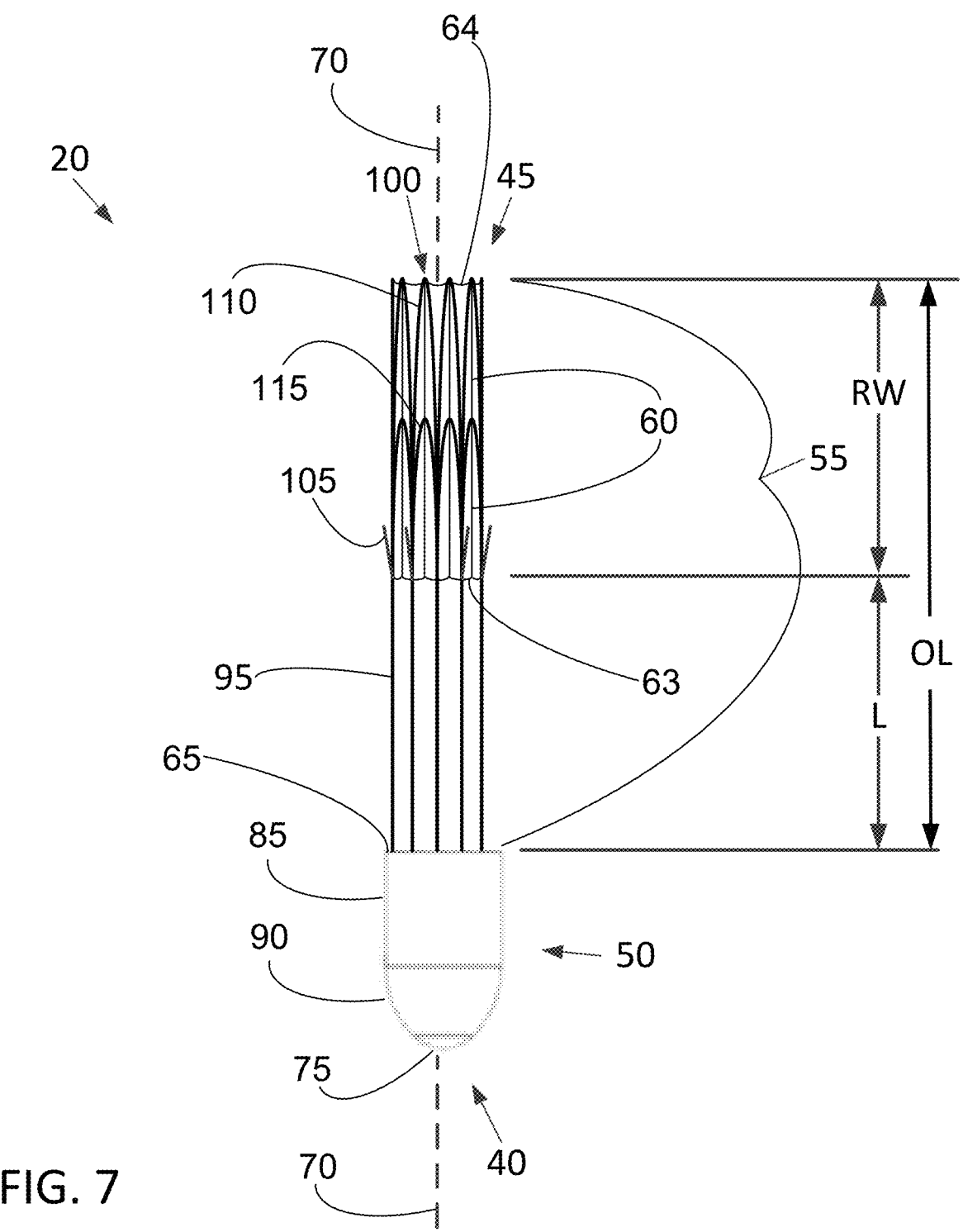
FIG. 7 is a side elevation view of the implantable cardiac valve repair implant in a collapsed state.

When in the collapsed state, as depicted in FIG. 7, which is a side view of the implant collapsed to allow its delivery to the target site via the tool 15, the frame 55 and thin sheet 60 collapse symmetrically about the central longitudinal axis 70. Thus, a comparison of the implant 20 in FIGS. 2-6 when in the expanded state to the implant 20 in FIG. 7 in the collapsed state indicates that the implant can transition from the collapsed state to the expanded state similar to an umbrella.

As can be understood from FIG. 9 and discussed in greater detail later in this Detailed Disclosure, during delivery, the implant 20 is maintained in the collapsed state of FIG. 7 by the tool 15 so as to allow the implant to be negotiated through the patient vascular system and into an atrial chamber of the heart for implantation of the implant within a target cardiac valve. For example, with the implant 20 maintained in the collapsed state by virtue of being confined within a tubular sheath 76 of the delivery tool 15, the implant may be delivered and deployed at the target site via an antegrade percutaneous route (e.g., an antegrade trans-femoral or trans-jugular route) with the patient consciously sedated during the procedure.

Upon being properly positioned in the target cardiac valve for repair, the physician actuates the tool 15 such that the tool no longer maintains the implant 20 in the collapsed state, as can be understood from FIG. 1A. Since the frame 55 of the implant 20 is biased to self-expand into the expanded state of FIGS. 2-6, the implant self-expands into the expanded state to anchor itself within the target cardiac valve and reduce regurgitation, as shown in FIG. 10.

Returning to FIGS. 2-6, it can be understood that the central occluder 50 may take the form of a bullet or conical shape. In doing so, the central occluder may have a cylindrical side 85 extending distally from the central occluder proximal end 65 and then transitioning to a bullnose 90 that distally extends to the central occluder extreme distal tip 75. Such a bullet or conical shape results in the central occluder 50 being atraumatic for delivery and implantation purposes. Further, such a shape facilitates the cylindrical side 85 of the central occluder substantially sealing against the cardiac valve leaflets, thereby materially reducing, if not eliminating, central regurgitation past the cardiac valve leaflets.

Without limitation and depending on the embodiment, the central occluder 50 may be formed from polytetrafluoroethylene (PTFE), polyether ether ketone (PEEK), acetal, silicone, nylon, polyethylene, polypropylene, polyethylene terephthalate (PET), polyurethane, or other thermoplastic elastomers. In certain embodiments, the material of the central occluder 50 may be angio- and/or echolucent.

In certain embodiments, the central occluder 50 may be filled with saline, a combination of saline with a radio-opaque contrast agent, or other fluid. In such embodiments, the central occluder 50 may be delivered in a first configuration having a reduced diameter and then expanded into a second configuration having an increased diameter by introducing fluid into the central occluder 50 following delivery. The amount of saline delivered during implantation may be determined in real-time, for example, by monitoring a size of the central occluder 50, e.g., using an X-ray image, and/or by monitoring a reduction of regurgitation, e.g., using ultrasound imaging.

Figure 5:
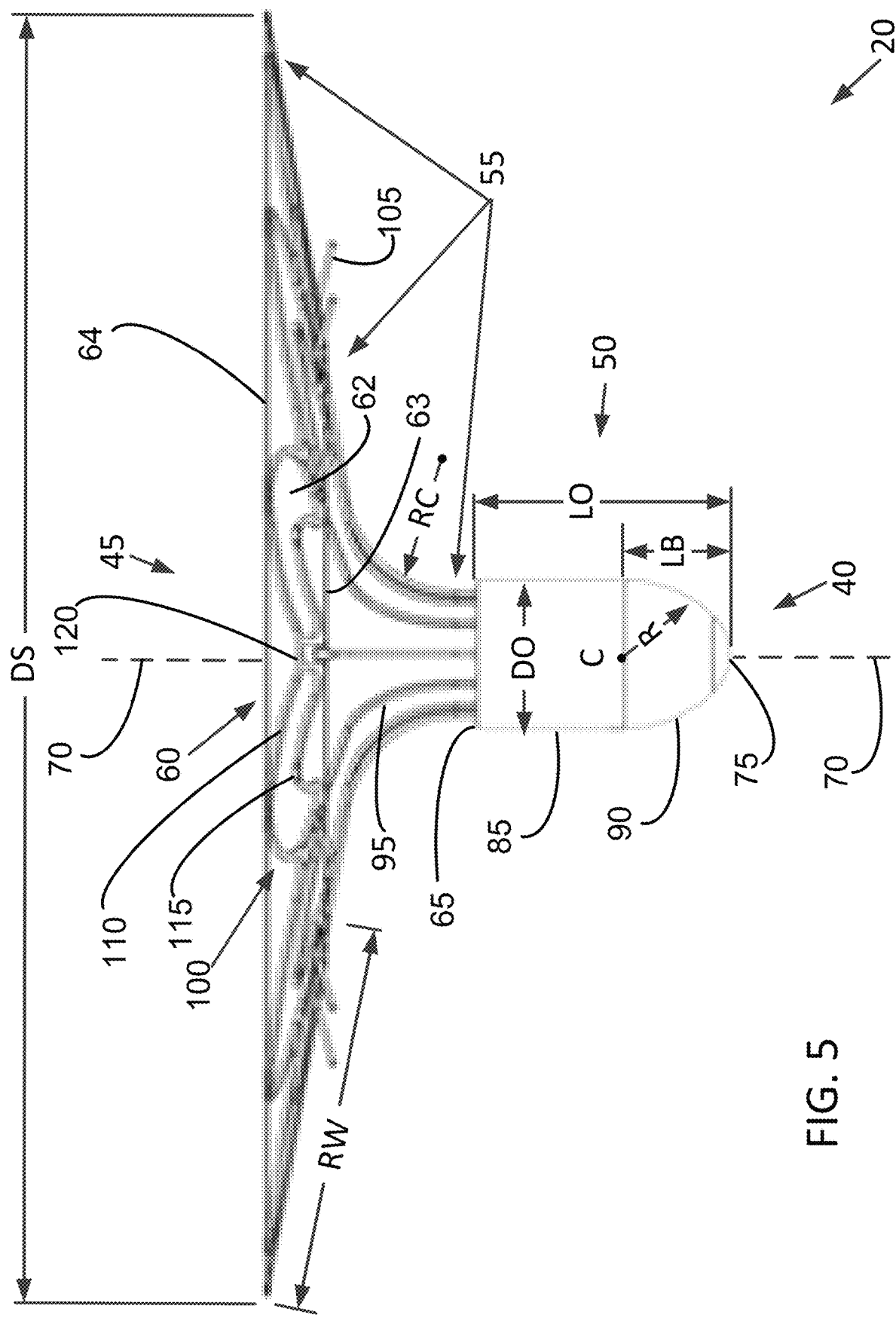
FIG. 5 is a side elevation view of the implantable cardiac valve repair implant in the expanded state.

In certain embodiments and without limitation, the central occluder 50 may be formed from a material having a durometer from and including 10A to and including 100D, from and including 10D to and including 100D, or from and including 40D to and including 80D. In one specific embodiment, the material of the central occluder 50 has a durometer of 80D. As indicated in FIG. 5, the central occluder may have an overall diameter DO that, in certain embodiments and without limitation, may be between approximately 5 millimeters (mm) and approximately 25 mm, between approximately 5 mm and approximately 15 mm, or between approximately 8 mm and approximately 12 mm. The central occluder 50 further has an overall length LO from its proximal end 65 to its extreme distal tip 75 that, in certain embodiments and without limitation, may be between approximately 5 mm and approximately 40 mm or between approximately 10 mm and approximately 20 mm. The bullnose 90 may have a length LB that, in certain embodiments and without limitation, may be between approximately 2.5 mm and approximately 12.5 mm, between approximately 2.5 mm and approximately 7.5 mm, or between approximately 4 mm and approximately 6 mm. In certain embodiments and without limitation, the radius of curvature R of the bullnose 90 may be between approximately 2.5 mm and approximately 12.5 mm, between approximately 2.5 mm and approximately 7.5 mm, or between approximately 4 mm and approximately 6 mm. The general shape of the bullnose 90 may also vary across embodiments. For example, the bullnose 90 may have any of a parabolic profile, a conical profile, a spherical profile, or any other atraumatic profile. In other example embodiments, the bullnose 90 may have a trihedral, frustoconical shape, or other non-rounded shape. In certain example embodiments, the central occluder 50 may have a triangular or tri-lobe shape that provides surfaces for sealing against respective leaflets. In yet another example, the central occluder 50 may have a rounded double-concave shape. In still other embodiments, the central occluder 50 may be configured to allow distention of a distal portion of the frame 55, thereby facilitating reintervention (e.g., valve implantation). In yet other embodiments, the central occluder 50 may include a frame (e.g., inner struts) covered in a flexible material, such as, but not limited to expanded polytetrafluoroethylene (ePTFE), polyester fabric, or a similar material. In such embodiments, the flexible covering may allow the central occluder 50 to be compressed for delivery but to expand once positioned in the native valve to occlude and reduce regurgitation.

As can be understood from FIG. 5, in one embodiment, the central occluder 50 may have an overall diameter DO of approximately 10 mm, and its overall length LO may be approximately 16 mm. Additionally, the bullnose 90 may have an overall length LB of approximately 5 mm, and the radius of curvature of the bullnose 90 may or may not gradually transition over its length LB from proximal to distal. For example, the radius of curvature R may have a maximum value from approximately 2.5 mm to approximately 15 mm as measured from a center of curvature C to the distal tip 75 of the central occluder 50 but may transition to a radius of curvature R that is between approximately 2.5 mm and approximately 10 mm, but less than or equal to the maximum, at a location proximal the distal tip 75. In one embodiment, however, the bullnose 90 may have a constant radius of curvature of approximately 5 mm.

As can be understood from FIGS. 2-6, the thin sheet 60 is supported on the frame 55 and secured thereto via. For example and without limitation, in certain embodiments the thin sheet 60 may be secured to the frame 55 by suturing the skirt against an inner surface and/or an outer surface of the frame 55. In other implementations, the thin sheet 60 may include a cuff or similar folded structure that is folded over an end of the frame 55. In still other implementations, the thin sheet 60 may be secured to the frame by sewing, welding, gluing/adhering, stapling, or any other suitable securement method or combination of securement methods. Depending on the embodiment, the thin sheet 60 may be on the distal side of the frame 55, the proximal side, or both such that the frame extends through and along the thin sheet. In one embodiment, the frame 55 is covered with a thin sheet 60 on the distal side of the frame where the frame contacts atrial tissue when the implant 20 is implanted in the target cardiac valve.

Depending on the embodiment, the thin sheet 60 may be formed of or include a woven or knit material or fabric that encourages tissue ingrowth. The porosity of the fabric of the thin sheet 60 assists in reducing commissural tricuspid regurgitation. Further reduction of commissural tricuspid regurgitation is provided by the angulation of the frame 55, which provides close contact with the commissures in a circumferential manner. For example, with the implant 20 implanted in the target cardiac valve, tissue in-growth into the fabric of the thin sheet 60 buttresses the myocardium, helping to keep the tissue from expanding further and reducing the potential of future regurgitation.

The fabric can be made from various methods, i.e. knitting, weaving, single or multiple layers. These fabrics can be laminated together with a polymer to make a composite structure, i.e. two pieces of knit (high porosity) with a polymer coating like silicone or urethane. Example materials for the woven or knit materials may include, without limitation, polyester, polypropylene, polyethylene, etc. The thin layer 60 may have a material thickness of between approximately 0.03 mm and approximately 1 mm, between approximately 0.05 mm and approximately 0.2 mm, or between approximately 0.07 mm and approximately 0.12 mm. In one example embodiment, the thickness of the thin layer 60 is approximately 0.2 mm. In another example embodiment, the thickness of the thin layer 60 is approximately 0.55 mm. In one embodiment, an additional textile layer may be added on the proximal side of the thin sheet 60 to create a smooth surface to minimize clot formation in an atrial chamber immediately adjacent the cardiac valve in which the implant 20 is implanted.

As indicated in FIGS. 5, 6 and 7, the thin sheet 60 has an outer diameter DS. In certain embodiments, the outer diameter DS may be between approximately 40 mm and approximately 80 mm, between approximately 50 mm and approximately 70 mm, or between approximately 55 mm and approximately 65 mm. The thin sheet 60 has a radial width RW. In certain embodiments, the radial width RW may be between approximately 10 mm and approximately 30 mm, between approximately 13 mm and approximately 23 mm, or between approximately 17 mm and approximately 19 mm. The thin sheet 60 has a central opening 66 with an inner diameter DI. In certain embodiments, the inner diameter DI may be between approximately 20 mm and approximately 60 mm, between approximately 25 mm and approximately 45 mm, or between approximately 28 mm and approximately 32 mm. For example, In one embodiment, the thin sheet 60 has an outer diameter DS of approximately 60 mm, a radial width RW of approximately 18.2 mm, and a central opening 66 with an inner diameter DI of approximately 30 mm. Due to its configuration, when the implant 20 is implanted in the target cardiac valve, the circumferential fabric of the thin sheet 60 covers a portion of the outer leaflet commissures to block leaks at the edges of the commissures.

As shown in FIGS. 2-6, the frame 55 includes spokes 95, arcuate petal portions 100 and protruding anchor members 105. The frame 55 may be made from a variety of super-elastic and/or shape memory materials, including, for example, nickel-titanium alloys (e.g., Nitinol), which may be laser cut from a tube or in the form of drawn wire. The features defined in the shape memory materials may be defined therein via various cutting methods known in the art, include laser, water jet, electrical discharge machining (EDM), stamping, etching, milling, etc.

In one embodiment, the frame 55 is made of super-elastic, shape memory nickel titanium alloy (e.g., Nitinol). Regardless of which shape memory material is employed, the shape memory aspects of the frame 55 allow the frame and, as a result, the implant 20 to self-bias from the collapsed state (see FIG. 7) to the expanded state (see FIGS. 2-6) when not physically maintained in the collapsed state by the delivery tool 15.

In various embodiments, the frame 55, central occluder 50 and the rest of the implant 20 remain implanted as a unit in the target cardiac valve. In other words, the implant 20 is implanted and remains so as configured in FIGS. 2-6.

There may be situations where it is desirable to remove the central occluder and then implant a replacement valve in the target cardiac valve. Accordingly, in alternate embodiments, the central occluder 50 and frame spokes or struts 95 may be removable after implantation, leaving the surrounding annular surface 62 of the implant in place, the annular surface 62 being formed by and including the frame arcuate petal portions 100 and the thin sheet 60 supported thereon. In such embodiments, a circumferential suture connection may exist between the spokes 95 and the rest of the frame 55 radially outward of the spokes 95. Thus, this circumferential suture connection may be cut and the central occluder 50 and its spokes 95 may be removed through a catheter, leaving the annular portion of the implant, which then acts as an "annuloplasty" frame.

As indicated in FIG. 7, when the implant 20 is in the collapsed state, the spokes 95 proximally extend from the proximal end 65 of the central occluder 50 to the arcuate petal portions 100. In doing so, the spokes 95 are substantially parallel with, and extend along and near to, the central longitudinal axis 70 of the implant 20. As can be understood from FIG. 7, when the implant is in the collapsed state, each spoke 95 has a length L from the central occluder proximal end 65 to a distal boundary of an arcuate petal portion 100. In certain embodiments, the length L may be between approximately 10 mm and approximately 40 mm or between approximately 15 mm and approximately 22 mm, with one embodiment having a length L of approximately 19 mm. As indicated in FIG. 7, the frame 55 in the collapsed state thus has an overall length OL that is the sum of the length L (shown in FIG. 7) and the radial width RW (shown in FIGS. 5 and 7), the candidate dimensions for the radial width RW being as discussed above with respect to FIG. 5.

As shown in FIGS. 2-6, when the implant 20 is in the expanded state, the spokes 95 proximally extend from the central occluder proximal end 65 and laterally radiate away from the central longitudinal axis 70 of the implant 20 to the arcuate petal portions 100. In doing so, the spokes 95 have a radius of curvature RC of between approximately 5 mm and approximately 20 mm, between approximately 10 mm and approximately 18 mm, or between approximately 15 mm and approximately 16 mm with one embodiment having a radius of curvature RC of approximately 15 mm, as can be understood from FIG. 5.

Depending on the embodiment, the frame 55 may include between approximately 3 and approximately 15 spokes 95. In certain embodiments, the number of spokes 95 and gaps therebetween may be selected to facilitate passage of other tools and devices past the frame 55. Embodiments may include spokes 95 with various cross-sectional shapes; however, in at least certain embodiments, spokes 95 have an annular sector cross-sectional shape, such as illustrated in Inset A-A of FIG. 6. In such embodiments, the cross-sectional shape of the spokes 95 may be defined by each of a strut width SW (defined as the maximum width of the spoke) and a wall thickness WT of the spokes 95. The spokes 95 may be further defined by a cross-sectional radius of curvature CSR as measured to a centerline CL of each spoke.

In certain implementations, the wall thickness WT may be between approximately 0.2 mm and 0.8 mm, between approximately 0.3 mm and approximately 0.7 mm, or between approximately 0.4 mm and approximately 0.6 mm. In addition, in certain implementations, the spokes 95 may conform to certain spoke aspect ratios, which, in the context of the spokes 95 refers to the ratio of the wall thickness WT to the strut width SW. For example, and without limitation, embodiments may have a spoke aspect between 4:0.5 and 1:2, between 3:1 and 1:1.2, or between 2:1 and 1:1. In embodiments, the cross-sectional radios of curvature CSR may be between approximately 2 mm and approximately 6 mm, between approximately 3 mm and approximately 5 mm, or between approximately 3.5 mm and approximately 5 mm. In one particular embodiment, the frame 55 is made of Nitinol and the frame 55 has 12 spokes 95, with each spoke 95 having a wall thickness WT of approximately 0.46 mm, an aspect ratio of approximately 2:1 (resulting in a strut width SW of approximately 0.23 mm), and a cross-sectional radius of curvature CSR of approximately 5 mm. In certain embodiments, the spokes 95 may be arranged such that they extend distally from the frame 55 at an angle such that the thin sheet 60 occludes coaptation gaps. In certain embodiments of the present disclosure, each of the spokes 95 may be dimensionally identical; however, in other embodiments, one or more of the spokes 95 may differ in any of the various characteristics noted above.

As illustrated in FIGS. 2-6, each arcuate petal portion 100 is located between a pair of spokes 95 and forms a section of the circumference of a radially outward half of the expanded frame 55. As can be understood from FIG. 5, unlike the spokes 95, which are curved in the expanded state, the arcuate petal portions 100 in the expanded state are generally straight in a laterally radiating direction and have approximately the same radial width RW as that of the thin sheet 60. Each petal portion 100 has an outer arcuate member 110 and an inner arcuate member 115, both of which point radially outward. These arcuate members 110, 115 intersect at a junction portion 120 that extends from a respective spoke 95 and surrounds a protruding anchor member 105 that distally projects from a distal side of its junction portion 120.

Depending on the embodiment, the frame 55 may include different numbers of petal portions 100. For example, in certain example embodiments, the frame 55 may include between 3 and 18 petal portions 100, between 6 and 15 petal portions 100, or between 10 and 14 petal portions 100. In one embodiment, the frame 55 has 12 petal portions 100. Similarly, the frame 55 may include different numbers of protruding anchor members 105. For example, in certain example embodiments, the frame 55 may include between 6 and 60 protruding anchor members 105, between 12 and 36 protruding anchor members 105, or between 18 and 30 protruding anchor members 105. In one embodiment, the frame 55 has 24 protruding anchor members 105.

The frame 55 engages the atrial tissue via the protruding anchor members 105, which may be in the form of small barbs. The protruding anchor members 105 are designed to securely engage the atrial tissue without penetrating through the tissue or to the coronary vessels. Depending on the embodiment, the protruding anchor members or barbs 105 may be curved to slide before engaging tissue. There may be one row or multiple rows of retention barbs 105.

As indicated in the enlarged view of a junction portion 120 of FIG. 6, each protruding anchor member 105 is defined in the surrounding junction portion 120 via a slot 125 that extends around the protruding anchor member 105 such that the anchor member 105 is peninsular in the surrounding junction portion 120. A radially inward end 105A extends uninterrupted to the rest of the surrounding junction portion 120 and is opposite a radially outward free end 105B of the anchor member 105, the radially outward free end 105B forming a tip of the protruding anchor member 105. As can be understood from FIGS. 2, 3 and 5, the radially outward free end of the anchor member projects distally from the rest of the frame 55.

Depending on the embodiment, each protruding anchor member 105 may have a length of between approximately 0.5 mm and approximately 6 mm, between approximately 1 mm and 4 mm, or between approximately 1 mm and approximately 3 mm. Similar to the spokes 95, the protruding anchor members 105 may have various cross-sectional shapes. In at least certain embodiments, the protruding anchor members 105 have an annular sector cross-sectional shape, similar to that discussed above in the context of the spokes 95 and as illustrated in Inset A-A of FIG. 6 and which is referenced for purposes of the following discussion. Like the spokes 95, the cross-sectional shape of the protruding anchor members 105 may be defined by each of a strut width SW (defined as the maximum width of the spoke) and a wall thickness WT. The protruding anchor members 105 may be further defined by a cross-sectional radius of curvature CSR as measured to a centerline CL of each anchor member. In certain implementations, the wall thickness WT may be between approximately 0.2 mm and 0.8 mm, between approximately 0.3 mm and approximately 0.7 mm, or between approximately 0.4 mm and approximately 0.6 mm. In addition, in certain implementations, the protruding anchor members 105 may conform to certain aspect ratios between the wall thickness WT to the strut width SW. For example, and without limitation, protruding anchor members 105 according to certain embodiments may have an aspect between 4:0.5 and 1:2, between 3:1 and 1:1.2, or between 2:1 and 1:1. In certain embodiments, the cross-sectional radios of curvature CSR may be between approximately 2 mm and approximately 6 mm, between approximately 3 mm and approximately 5 mm, or between approximately 3.5 mm and approximately 5 mm. Each protruding anchor member 105 has a wall thickness WT of approximately 0.46 mm, an aspect ratio of approximately 2:1 (resulting in a strut width SW of approximately 0.23 mm), a cross-sectional radius of curvature CSR of approximately 5 mm, and a length of approximately 1.5 mm. In certain embodiments of the present disclosure, each of the protruding anchor members 105 may be dimensionally identical; however, in other embodiments, one or more of the protruding anchor members 105 may differ in any of the various characteristics noted above.

Figure 2:
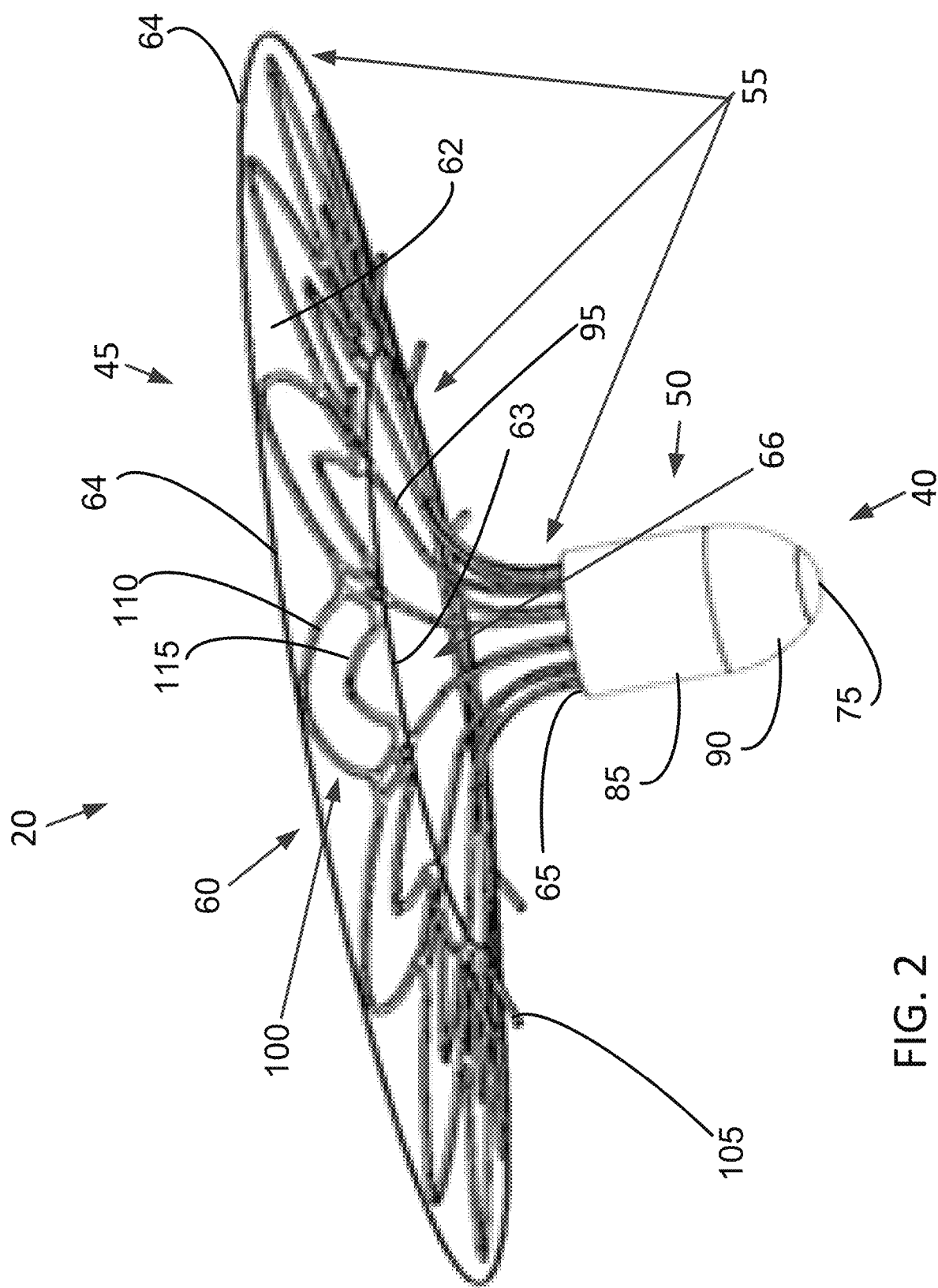
FIG. 2 is a perspective distal-side view of the implantable cardiac valve repair in an expanded state that is used when the implant is implanted in the cardiac valve.
Figure 3:
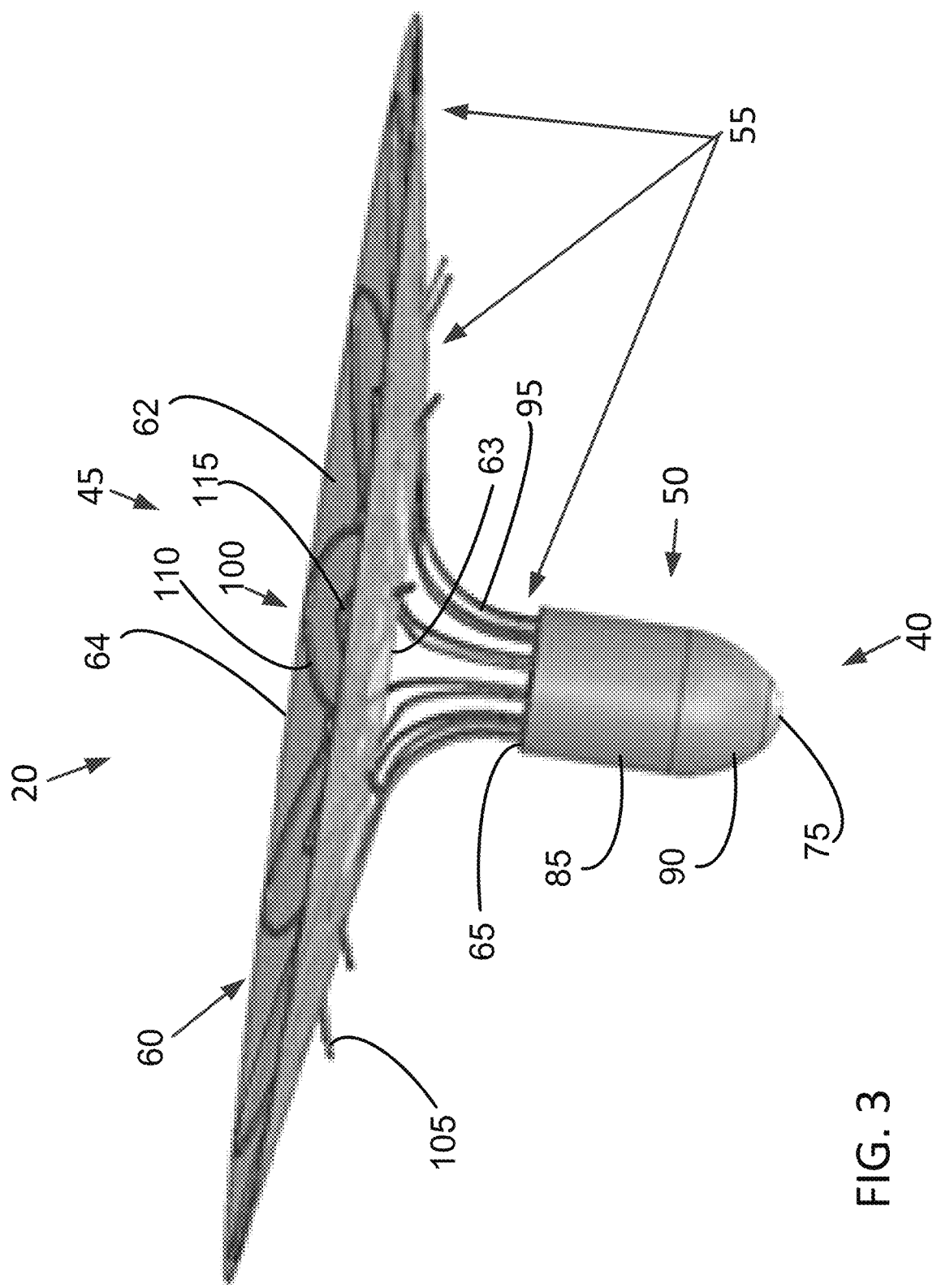
FIG. 3 is a perspective proximal-side view of the implantable cardiac valve repair implant in the expanded state.
Figure 4:
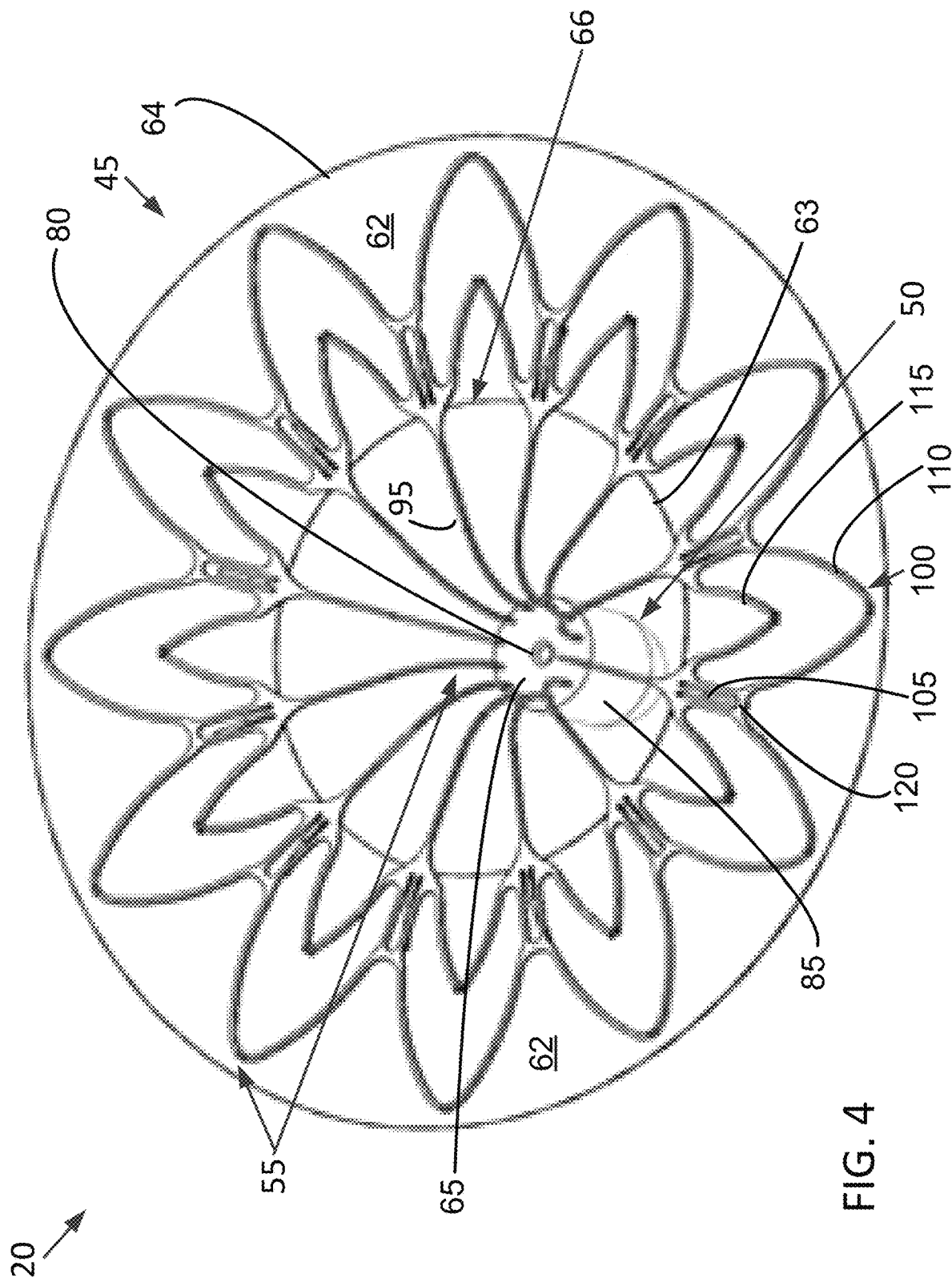
FIG. 4 is a perspective proximal-end view of the implantable cardiac valve repair implant in the expanded state.

In one embodiment, as can be understood from FIGS. 2, 3 and 5, the protruding anchor members or barbs 105 are oriented distally and radially outward. As a result, as the frame 55 is pushed towards the ventricle, the anchor members 105 slide along the atrial tissue. Ventricular pressure pushes the implant 20 towards the atrium, embedding the anchors or barbs 105 into the atrial tissue.

In an alternate embodiment, the anchors or barbs 105 are directionally reversed such that they project distally and radially inward. In this alternative embodiment, the delivery system over-expands the frame 55 during delivery and when the frame is released from the delivery system with the frame 55 in contact with tissue, the anchors or barbs 105 engage the atrial tissue as the frame 55 contracts to its relaxed state.

II. Delivery Tool and Method of Implantation

As illustrated in FIGS. 1A-1D, the delivery tool 15 includes a proximal end 30, a distal end 25 opposite the proximal end, a control handle 35, a tubular sheath 76, and a catheter 77. The control handle 35 extends distally from the proximal end 30 and is used by a physician to manipulate the tool 15 in positioning the implant 20 at the target site and deploying the implant 20 within the target cardiac valve in need of repair. The sheath 76 and catheter 77 extend distally away from the control handle 35 towards the distal end 25 of the tool 15. The catheter 77 extends longitudinally through the sheath 76, the distal end 25 of the catheter 77 forming the distal end 25 of the tool 15. The sheath 76 is used to minimize tissue trauma while the catheter 77 and implant 20 are advanced to the implantation site. Thus, the delivery tool 15 is designed to deliver the implant 20 to the implantation site, position the implant in the target cardiac valve, and control the opening of the frame 55 of the implant 20, all in an atraumatic manner.

Figure 8:
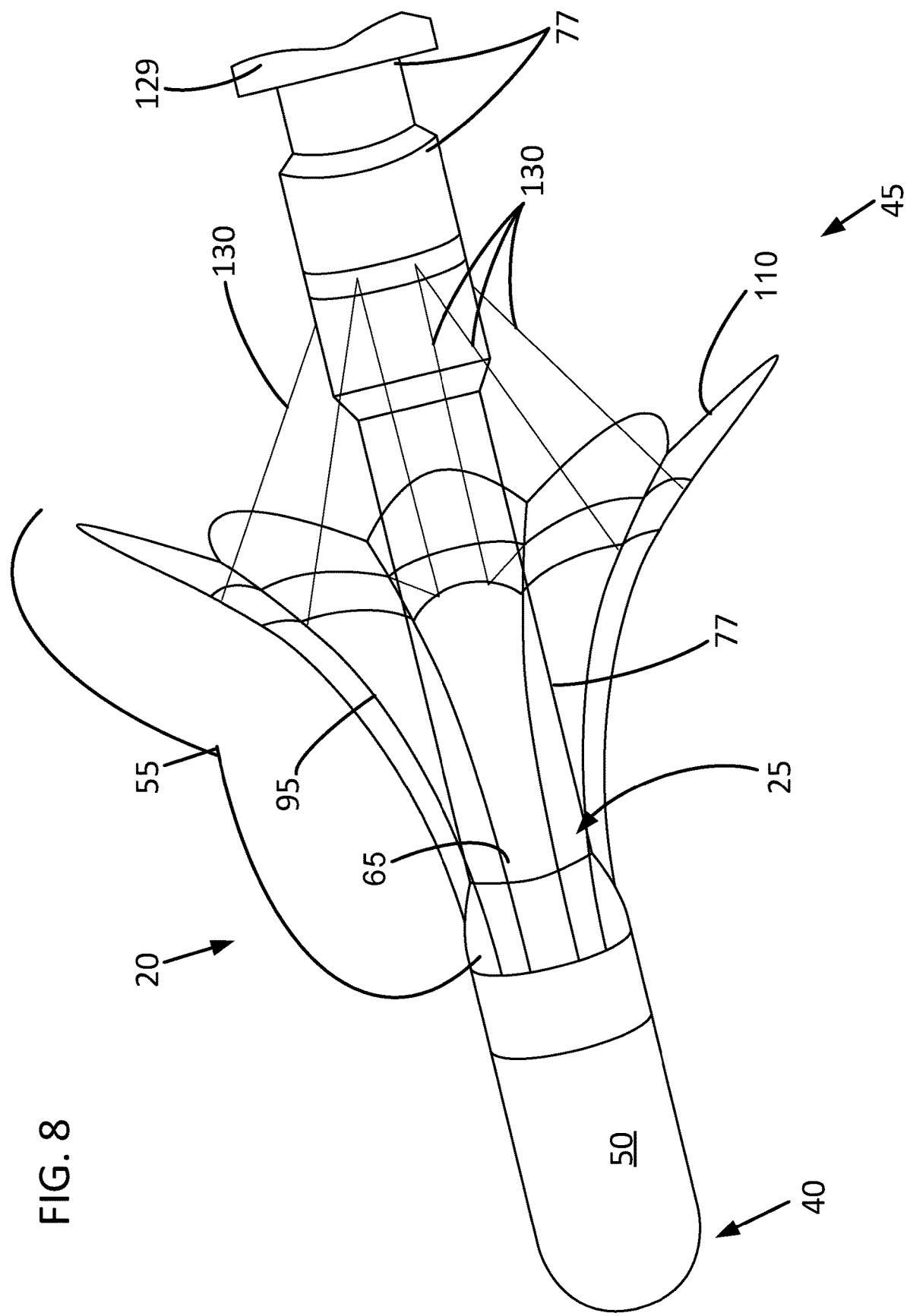
FIG. 8 is an enlarged view of the distal region of the cardiac repair system of FIG. 1A.

As depicted in FIG. 8, which is an enlarged view of the distal region of the cardiac repair system 10 of FIG. 1A, sutures 130 extend between a distal region of the catheter 77 and points of connection on the frame 55 of the implant 20. The sutures 130 further extend from the distal region of the catheter up into the handle 35 and, in one embodiment, may even extend out of the handle, as shown in FIG. 1A. Depending on the embodiment, the control sutures 130 could be replaced by cables or wire.

As can be understood from FIGS. 1A and 8, before the implant 20 is completely freed of the delivery tool 15, the sutures 130 can be manipulated via the handle 35 of the tool 15 to control the opening of the implant frame 55. Suture actuation may have one or two speeds, which may be in the form of a slow speed and/or a fast speed. The slower speed may be controlled by a spooling mechanism or a lead screw mechanism 135 within the handle. The fast speed may be controlled by a plunger style linear actuator 140 within the handle. The sutures 130 may be routed within the handle 35 to provide a 2-to-1 mechanical advantage to facilitate increased precision of control when deploying the implant 20.

The catheter 77 may employ steering via selective actuation (e.g., tension increase/decrease) of certain sutures to better control the position of the implant during deployment. This steering feature may be controlled at the handle 35.

Figure 9:
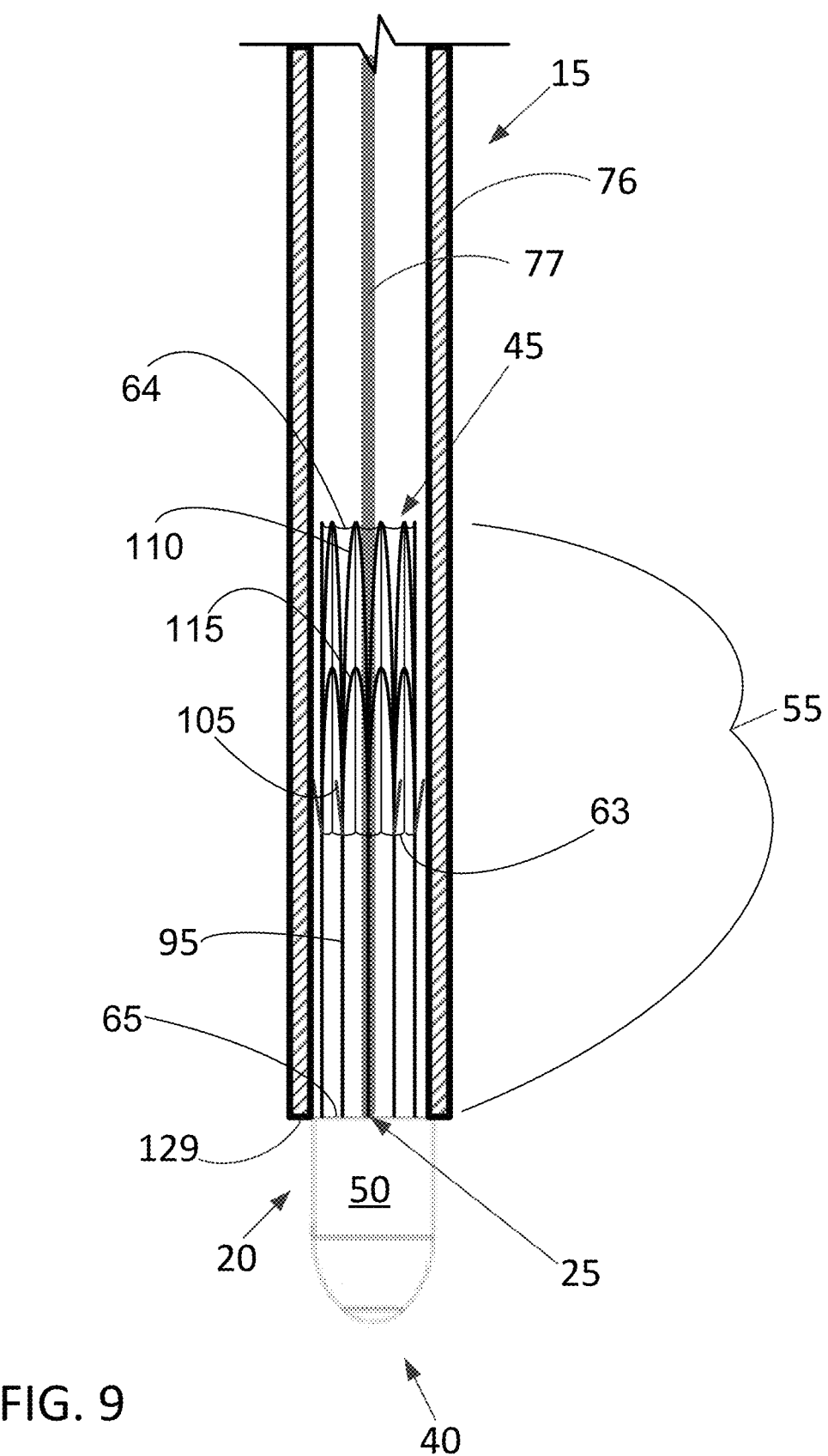
FIG. 9 is a side cross-sectional elevation view of a sheath of the delivery tool with the implantable cardiac valve repair implant maintained in the collapsed state by being confined within the sheath, the implant being coupled to a distal end of a catheter that extends through the sheath.

FIG. 9 is a side cross-sectional elevation view of the sheath 76 of the delivery tool 15 with the implantable cardiac valve repair implant 20 and distal region of the catheter 77 located therein. As can be understood from FIG. 9, during delivery the implant 20 is maintained in the collapsed state by being confined within the sheath 76, and the implant 20 is coupled to a distal end of a catheter 77 that extends through the sheath 76. The control sutures 130, while not shown in FIG. 9 for clarity purposes, would extend through the catheter 77 and/or the sheath 76, as can be understood from FIGS. 1A and 8.

With the implant 20 maintained in the collapsed state by virtue of being confined within the sheath 76 of the delivery tool 15, the implant may be delivered and deployed at the target site via an antegrade percutaneous route (e.g., a trans-femoral or trans-jugular route) with the patient consciously sedated during the procedure. A distal end 25 of the catheter 77 is coupled with the proximal end 65 of the central occluder 50 to maintain the implant 20 within the sheath 76 in the collapsed state until the physician decides to deploy the implant within the target cardiac valve.

Upon the implant being properly positioned in the atrium and beginning to approach the target cardiac valve for repair, the physician actuates the tool 15 to cause the catheter 77 to act as a plunger and/or stopper, thereby driving the collapsed implant 20 distally from the confines of the sheath 76 and/or allowing the sheath 76 to be withdrawn proximally from about the implant 20. Upon the collapsed implant 20 becoming exposed by action of exiting the distal end 129 of the sheath, the implant 20 self-biases into its expanded state, as depicted in FIGS. 2-6. However, as indicated in FIG. 8, despite having exited the sheath distal end 129 and assuming the expanded state, the proximal end 65 of the central occluder 50 of the implant 20 remains coupled to the catheter distal end 25 and the implant frame 55 is coupled to the sutures 130, thereby allowing the physician to use the delivery tool 15 to drive the implant into the target valve and manipulate the implant therein for implantation.

The configuration of the implant 20 facilitates delivery and implantation that is very easy and fast. The implant's ease of delivery is facilitated by it generally only requiring the user to approximately center the frame and push it into the valve.

Upon arrival of the implant 20 within the atrium and at the target cardiac valve, the physician simply uses the tool 15 to actuate the sutures 130 to allow the frame 55 to self-bias open over the atrial side of the target cardiac valve in a controlled manner. The catheter 77 of the tool 15 is then used to push the implant 20 towards the ventricle to engage the frame barbs 105 into the atrial tissue surrounding the target cardiac valve. The control sutures 130 can be used to collapse the frame 55 of the implant 20 to facilitate repositioning of the implant if necessary. Once the implant is fully implanted as desired by the physician, the exposed ends of the control sutures 130 are cut near their points of securement to the implant frame 55, and the catheter distal end 25 is released (e.g., unscrewed or otherwise decoupled) from the proximal end 65 of the central occluder 50. With the tool 15 so decoupled from the implanted implant, the tool can be withdrawn from the patient.

FIG. 10 is a view of the implant 20 implanted in a target cardiac valve, as viewed from an atrial position looking towards the valve and the ventricle chamber below. As depicted in FIG. 10, upon being implanted in the target cardiac valve, the implant anchors itself within the target cardiac valve and is configured to reduce regurgitation in the target cardiac valve. When implanted, the implant 20 is located on the atrial side of the target cardiac valve. The frame engages the atrial tissue via the small barbs 105. The thin sheet 60, which is supported on the frame 55, forms an annular surface 62 supported on the expanded frame 55. This annular surface 62 extends across the atrial tissue circumferentially around the circumference of the target cardiac valve. The central occluder 50 is suspended off the frame 55 and located in the middle of the valve orifice or opening. So positioned, the implant provides the following advantages and reduces regurgitation through multiple mechanisms-of-action.

First, the metal frame 55 supports a central occluder 50 that is positioned to block a central leak in the target cardiac valve, the central occluder thereby reducing central regurgitation through the target cardiac valve. Specifically, the central occluder may block part or all of the central regurgitation in the valve.

Second, the thin sheet 60 covering the frame 55 encourages ingrowth with the atrial and annular tissue surrounding the target cardiac valve. With such tissue ingrowth, the thin sheet and its supporting frame 55 can act as an annuloplasty ring to buttress the native tissue and reduce myocardial stretching that could increase regurgitation.

Third, the thin sheet 60 covering the frame 55 may overlap the edges of the leaflet commissures, reducing the possibility of commissural leak.

Finally, the frame 55 may be over-expanded before engaging the retention barbs 105 in the tissue. When the frame is allowed to relax, the frame 55 may reduce the valve orifice of the target cardiac valve and improve apposition of the valve leaflets, thereby reducing or eliminating regurgitation.

III. Steerable Delivery Tool

FIGS. 11A and 11B are plan and side elevation views, respectively, of an alternative valve repair system 1100 according to the present disclosure. Similar to valve repair systems previously discussed herein, the valve repair system 1100 is generally configured to deliver and deploy an implant 20 at a target site, which is generally in a cardiac valve requiring repair. Embodiments of the valve repair system 1100 may be used with, but are not limited to being used with, any implants discussed herein or that are otherwise consistent with this disclosure.

As shown in FIGS. 11A and 11B, the valve repair system 1100 includes a delivery tool 1115. The tool 1115 includes a proximal end 1130 opposite a tool distal end 1125. The delivery tool 1115 further includes a tubular sheath 1176, and a catheter 1177. A control handle 1135 extends distally from the proximal end 1130 and is used by a physician to manipulate the tool 1115 in positioning the implant 20 at the target site and deploying the implant 20 within the target cardiac valve in need of repair. The sheath 1176 and catheter 1177 extend distally away from the control handle 1135 towards the distal end 1125 of the tool 1115. The catheter 1177 extends longitudinally through the sheath 1176, the distal end 1125 of the catheter 1177 forming the distal end 1125 of the tool 1115. The sheath 1176 is used to minimize tissue trauma while the catheter 1177 and implant 20 are advanced to the implantation site. Thus, the delivery tool 1115 is designed to deliver the implant 20 to the implantation site, position the implant in the target cardiac valve, and control opening of the implant 20, all in an atraumatic manner.

Figure 11C:
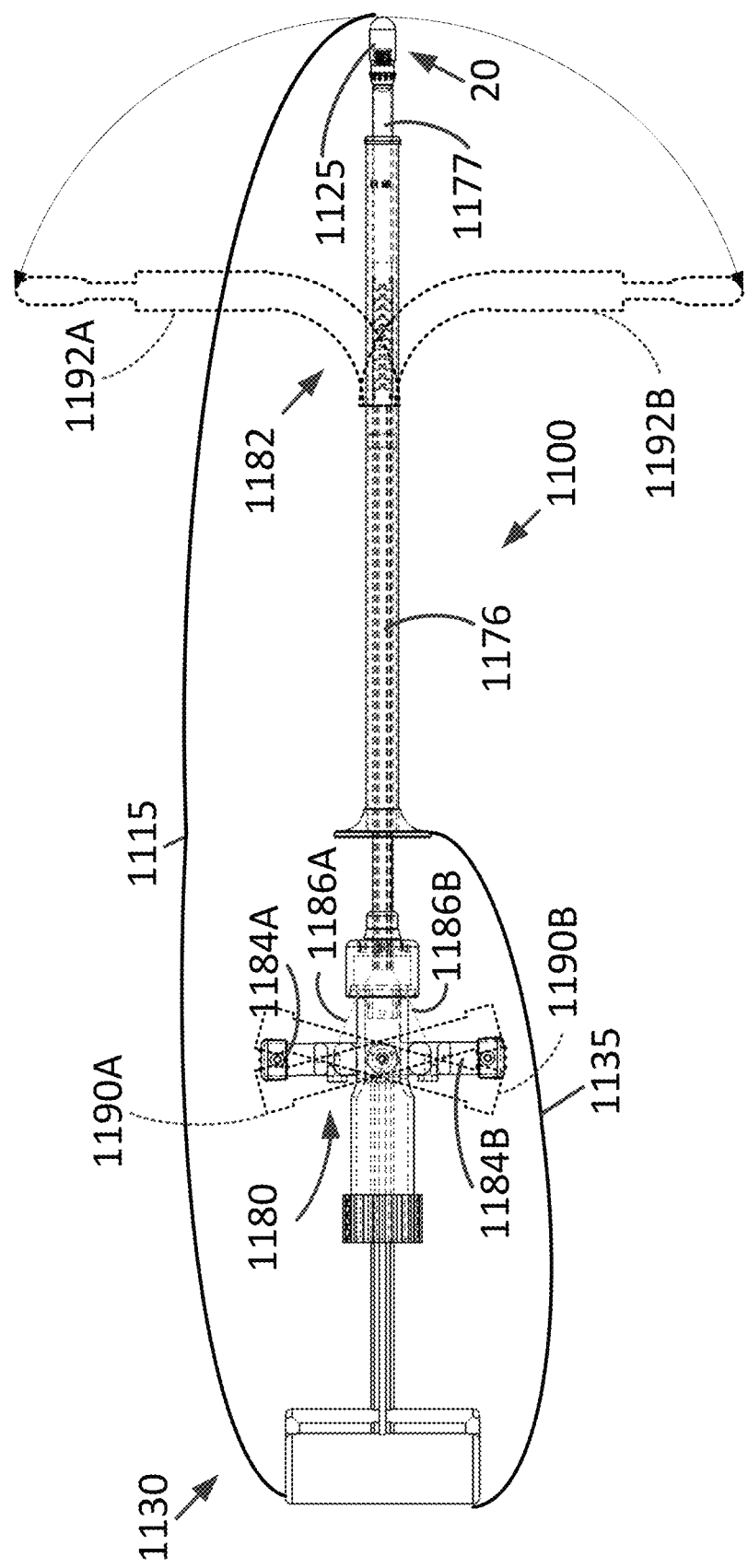

To facilitate delivery of the implant 20 to the implantation site, the catheter 1177 of the tool 1115 may be steerable. In the specific implementation illustrated in FIGS. 11A and 11B, for example, the control handle 1135 of the tool 1115 includes a bidirectional steering control 1180 that may be rotated to steer the distal end 1125 of the tool 1115. As illustrated in FIG. 11C, the steering control 1180 may be rotatable between two extents, illustrated by dashed outlines 1190A, 1190B, to steer the distal end 1125 between corresponding extents, illustrated by dashed outlines 1192A, 1192B. In the specific example illustrated, the steering control 1180 facilitates steering of the distal end 1125 across a range of motion of approximately 180 degrees. Stated differently, the steering control 1180 may rotate the distal end 1125 between a first position in which the distal end 1125 points in a first lateral direction and a second position in which the distal end points in a second lateral direction that is opposite the first lateral direction.

In certain embodiments, steering of the distal end 1125 is achieved by coupling the steering control 1180 to a steering segment 1182 disposed along the catheter 1177, distal the steering control 1180. More specifically, the steering control 1180 may include lateral members 1184A, 1184B, each of which is coupled to a respective side of a distal end of the steering segment 1182 by respective pull wires 1186A, 1186B. Accordingly, when the steering control 1180 is rotated, the corresponding pull wire is pulled and the steering segment 1182 is made to bend in the same direction. For example, referring to FIG. 11C, when the steering control 1180 is rotated counterclockwise with respect to the view of FIG. 11C, as illustrated by dashed outline 1190A, the lateral member 1184A pulls the pull wire 1186A, resulting in the distal end 1125 curling in a counterclockwise direction, as illustrated by dashed outline 1192A. Similarly, when the steering control 1180 is rotated clockwise with respect to the view of FIG. 11C, as illustrated by dashed outline 1190B, the lateral member 1184B pulls the pull wire 1186B, resulting in the distal end 1125 curling in a clockwise direction, as illustrated by dashed outline 1192B.

The steering segment 1182 may take various forms; but, in general, is a flexible and manipulable segment of the catheter 1177 or a separate sleeve or sheath coupled to the catheter 1177. In certain embodiments, for example, the steering segment 1182 may be a sleeve or a portion of the catheter 1177 that is formed from a flexible material. In other embodiments, the steering segment 1182 may be segmented or otherwise include slits, cutouts, or similar voids along its length to provide flexibility. In one specific implementation, the steering segment 1182 may have a helical shape. In still other embodiments, the steering segment 1182 may be have a segment of the catheter 1177 having a reduced wall thickness. The foregoing are merely examples and other techniques for forming the steering segment 1182 that may be used are contemplated.

In certain embodiments, the pull wires 1186A, 1186B are run within an annular space defined between the sheath 1176 and the catheter 1177. Alternatively, the pull wires 1186A, 1186B may be run through a lumen defined within a wall of the catheter 1177, a wall of the sheath 1176, or a third annular body disposed along the distal length of the tool 1115. For example, the catheter 1177 or an additional tubular sheath disposed between the catheter 1177 and the sheath 1176 may be formed as a triple lumen extrusion including a central lumen and a pair of smaller lumens disposed on opposite sides of the central lumen and through which the pull wires 1186A, 1186B extend.

Although illustrated in FIG. 11C as having a 180-degree range of motion, embodiments of the present disclosure may be configured to have other ranges of motions. For example, certain embodiments may be configured to rotate the distal end 1125 through 360 degrees of rotation, e.g., from a first position in which the distal end 1125 points proximally on a first side of the tool 1115 to a second position in which the distal end 1125 also points proximally on a second side of the tool 1115 opposite the first side. In other embodiments, the distal end 1125 may have a reduced range of motion such as but not limited to 135 degrees, 90 degrees, 45 degrees, or 15 degrees. In addition, while the range of motion illustrated in FIG. 11C is illustrated as being substantially even in both directions, embodiments of the present disclosure may have ranges of motion that are uneven in different directions. For example, a tool with a 135-degree range of motion may travel 90 degrees in a first direction but only 45 degrees in a second direction opposite the first direction. Moreover, while the tool 1115 has a neutral position in which the catheter 1177 is substantially straight, the catheter 1177 may alternatively be configured to have a bias in a particular direction.

IV. Implant with Tension Control Line

Figure 12:
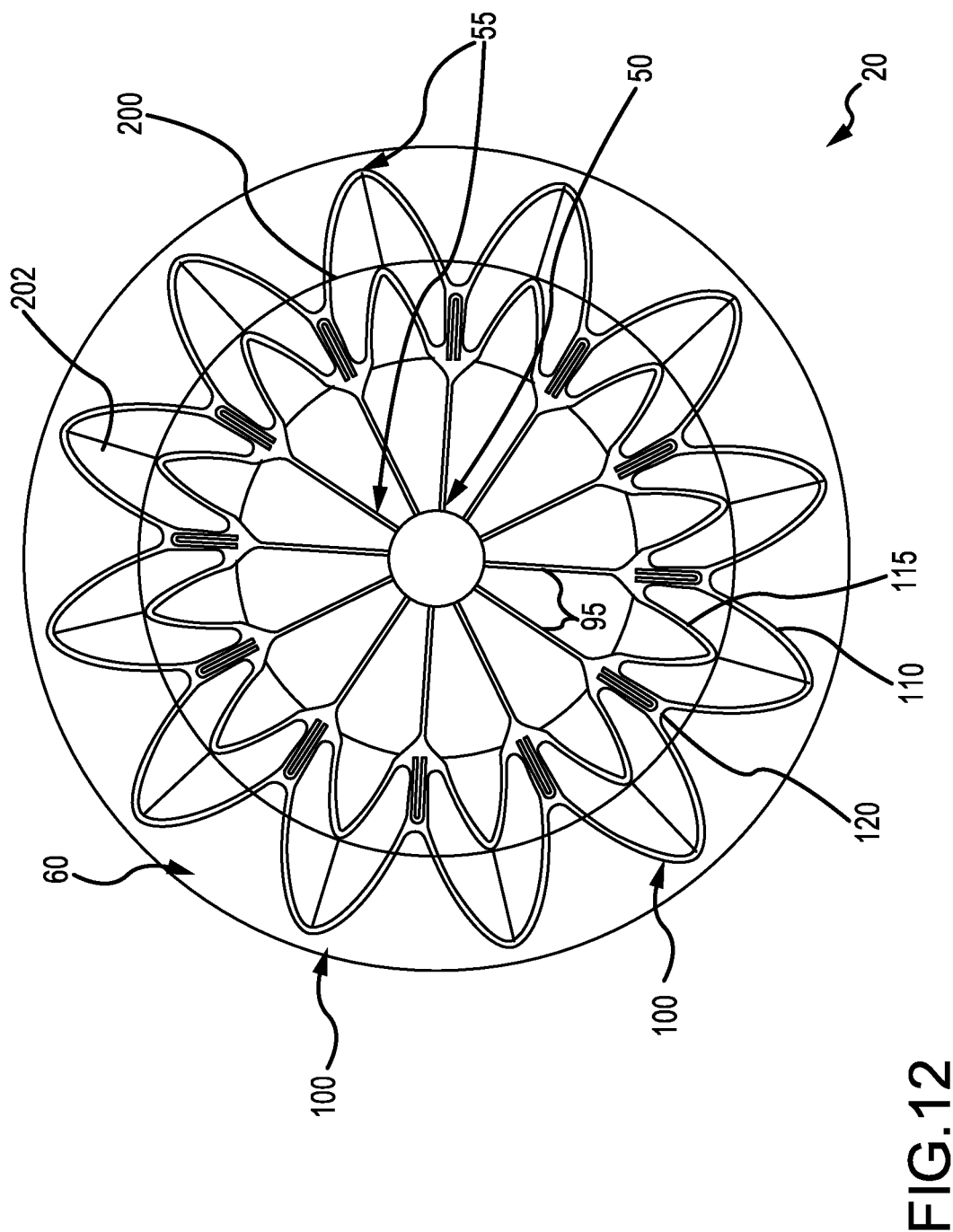
FIG. 12 is a distal plan view of an implantable cardiac valve repair implant in the expanded state and including a tension control line.

FIG. 12 is a distal plan view of the implant 20 in an expanded state and incorporating a tension control line 200. As previously discussed in the context of FIGS. 2-6, the implant 20 generally includes a central occluder 50, a frame 55 and a thin sheet 60 supported on the frame 55. Further details regarding the components and construction of the implant 20 and the frame 55 are provided above in the context of FIGS. 2-6.

As illustrated in FIG. 12, the tension control line 200 may be in the form of a wire, suture, cord, or similar elongate body coupled to the frame 55 and radially inward of the thin sheet 60 relative to the longitudinal axis 70 (shown in FIG. 5) of the implant 20. The tension control line 200 may form a loop extending around the frame 55 and may be formed from a single length of wire, suture, etc. In other implementations, the tension control line 200 may instead be formed from multiple discrete segments of wire, suture, etc., with each discrete segment coupled to the frame 55 and optionally coupled to adjacent segments of the control line 200.

During operation and, more specifically, during deployment of the implant 20, the tension control line 200 is releasably coupled to tension control members (e.g., tension control members 320 illustrated in FIGS. 13-22 and discussed below in further detail) of a delivery tool (e.g., delivery tool 300, similarly illustrated in FIGS. 13-22 and discussed below). The tension control members may be coupled to a handle or similar actuatable component of the delivery tool (such as the handle 35 of the tool 15 previously discussed), to vary tension applied to the tension control line 200 by the tension control members. For example, rotating the handle 35 in a first direction may cause the tension control members to translate proximally/retract, thereby increasing tension on the tension control line 200, while rotating the handle 35 in an opposite direction may cause the tension control members to translate distally/extend, thereby reducing tension on the tension control line 200. Stated differently, manipulating the handle 35 in a first direction generally stops expansion of and/or collapses the frame 55 of the implant 20 (e.g., to allow repositioning of the implant 20) while manipulating the handle 35 in a second direction generally stops collapse of the frame and/or expands the frame 55, whether by action of the handle 35 or as a result of a bias of the frame 55 to into the expanded configuration.

In general, the tension control line 200 is releasably retained by the tension control members at discrete locations along the length of the tension control line 200. The tension control line 200, however, extends across the frame 55 and is coupled to the frame 55 at multiple locations. As a result, even though tension modifications may be applied at the connection point between the tension control members and the tension control line 200, tension is distributed relatively evenly across the tension control line 200 and the frame 55, thereby providing even expansion and collapse of the frame 55 and improved control during deployment and placement of the implant 20.

In the implementation of FIG. 12, the tension control line 200 is coupled to (e.g., tied or adhered to) the inner arcuate members 115 of the frame 55. More generally, the tension control line 200 may be coupled to any suitable portion of the frame 55 such that the tension control line 200 substantially extends about the frame 55. For example, and without limitation, in other implementations of the present disclosure, the tension control line 200 may instead be fixed to spokes 95, outer arcuate members 110, or any other suitable portion of the petal portions 100 of the frame 55.

In certain implementations, the tension control line 200 may be additionally coupled to other locations of the frame 55 by additional control segments or linking structures. For example, FIG. 12 illustrates the tension control line 200 coupled to the inner arcuate members 115 of the frame 55.

The tension control line 200 is further coupled to each of the outer outer arcuate members 110 by corresponding links, such as the link 202. Similar to the control line 200, the link 202 may be formed of wire, suture, or similar material and, in certain cases, may be formed of the same material as the control line 200. In operation, the link 202 helps to further distribute tension to the outer arcuate members 110 and, as a result, further improves control of expansion an collapse of the frame during deployment of the implant 20.

Although illustrated in FIG. 12 as coupling the tension control line 200 to the outer arcuate members 110, in other implementations, links may be used to couple the tension control line 200 to other elements of the frame 55 depending on how the tension control line 200 is configured. For example, in implementations in which the tension control line 200 is coupled to the outer arcuate members 110, links may be used to couple the tension control line 200 to the inner arcuate members 115.

V. Deployment of Implants with Tension Control Lines

As previously discussed, implants according to the present disclosure may include tension control lines for enhanced control during deployment and implantation. Such delivery and implantation may be further facilitated by corresponding delivery tools configured to modify and control tension applied to the tension control lines and to selectively release the implant when properly positioned.

FIG. 13 is an illustration including a delivery tool 300 in accordance with the present disclosure in a disassembled state. As illustrated, the delivery tool 300 generally includes a sheath 302, a release catheter 304, and a tension control assembly 306. An implant 20 including a tension control line 200 is also pictured. The sheath 302 generally forms an exterior of the delivery tool 300 and houses the other components during insertion into the patient. More specifically, the release catheter 304 is generally disposed within the sheath 302 and the tension control assembly 306 is, in turn, disposed within the release catheter 304.

As described below in further detail, the tension control line 200 of the implant 20 is releasably coupled to the tension control assembly 306 by the release catheter 304 and is maintained in a collapsed state within the sheath 302 during initial insertion into the patient. During deployment, the release catheter 304 is distally extended from the sheath 302, thereby allowing the implant 20 to expand. Subsequent control of expansion and collapse of the implant 20 is facilitate by tension control members 320 extending from the tension control assembly 306, which are coupled to the control tension control line 200 of the implant 20 by release lines 350 of the release catheter 304. Following location of the implant 20 within the patient, the release lines 350 are retracted to decouple the tension control members 320 from the tension control line 200, thereby releasing the implant 20.

Figure 15:
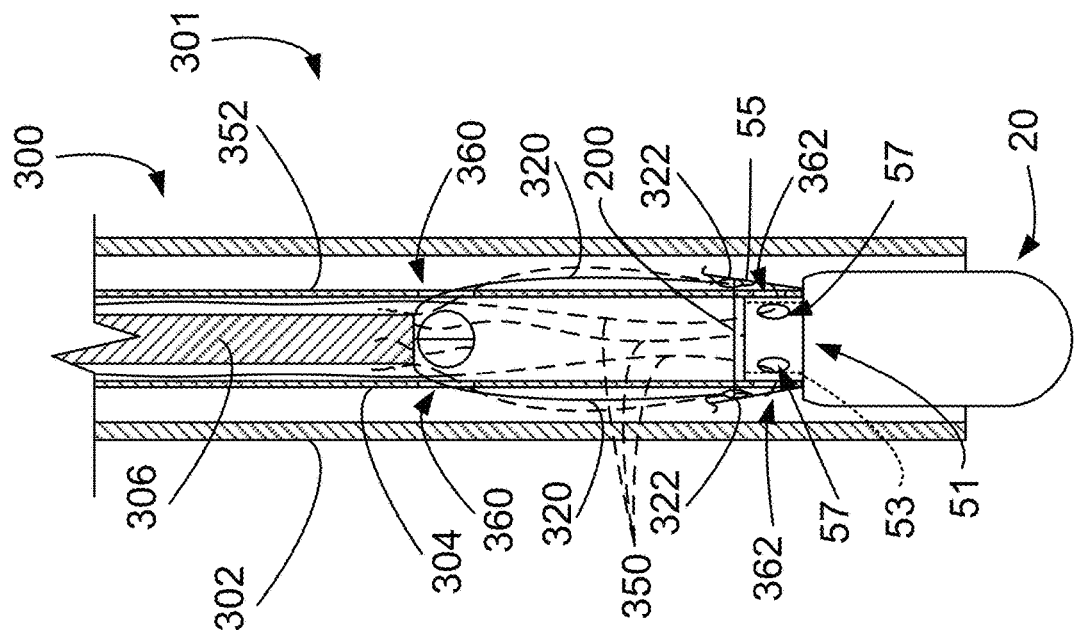
FIG. 15 is a side cross-sectional elevation view of a distal portion of the delivery tool of FIG. 13 coupled to the implant.
Figure 14:
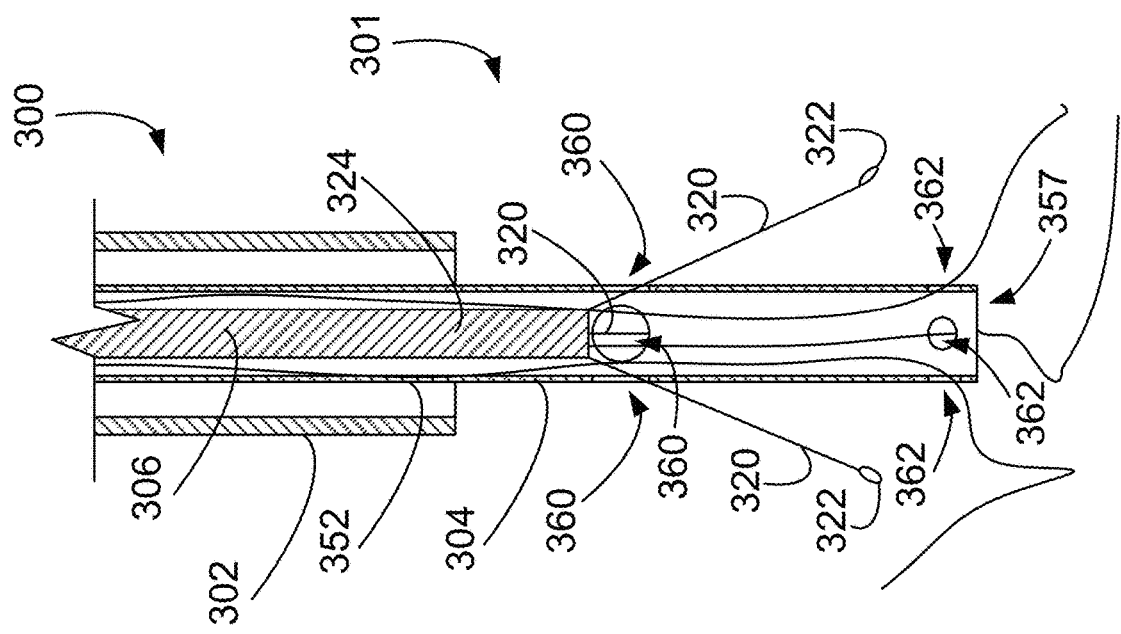
FIG. 14 is a side cross-sectional elevation view of a distal portion of the delivery tool of FIG. 13.

FIG. 14 is a cross-sectional view of a distal portion 301 of the delivery tool 300 in an assembled state and with each of the release catheter 304 and the tension control assembly 306 in an extended configuration for purposes of illustrating various elements of the delivery tool 300. FIG. 15 is also a cross-sectional view of the distal portion 301 of the delivery tool 300 but further includes an implant 20 and illustrates the delivery tool 300 in a retracted state, such as would be the case during initial insertion of the delivery tool 300 into the patient. For purpose of illustrating coupling of the implant to the release catheter 304, the frame 55 and associated components of the implant 20 are only partially illustrated in FIG. 15.

Figure 19:
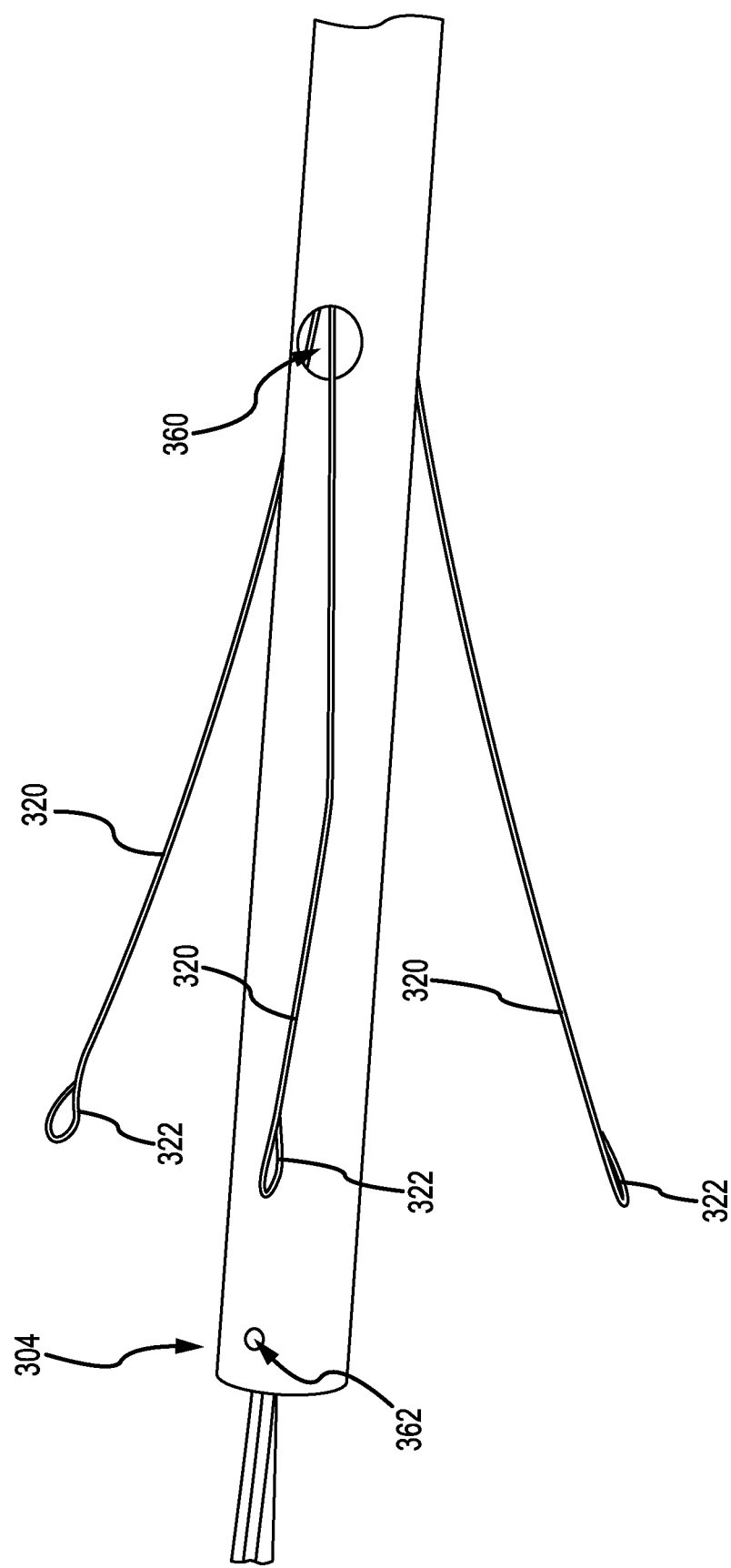
FIG. 19 is an illustration of a plan view of the delivery tool illustrating protrusion of tension control members through a release catheter of the delivery tool.

As previously discussed, tension control assembly 306 generally includes tension control members 320 that are releasably coupled to the control line 200 of the implant 20. As illustrated in FIGS. 14 and 15, the tension control members 320 may be in the form of cables, control sutures, wires, or similar elongate structures that extend distally from a distal end of a tension control shaft 324. In at least certain implementations, the tension control members 320 may terminate in a loop (e.g., loop 322) or similar structure to facilitate coupling of the tension control members 320 to the tension control line 200 of the implant 20. FIG. 19 is an illustration of the tension control assembly 306 disposed within the release catheter 304 with the tension control members 320 extending distally out of a catheter body 352 of the release catheter 304.

The release catheter 304 includes release lines 350 disposed within and extending through the catheter body 352. The catheter body 352 further defines two sets of lateral holes for facilitating tensioning and release functionality of the delivery tool 300. More specifically, the catheter body 352 defines a set of proximal holes 360 and a set of distal holes 362. The catheter body 352 further defines a distal opening 357. As illustrated in FIGS. 14 and 19, the tension control assembly 306 is generally assembled with the release catheter 304 such that the tension control members 320 extend distally through the proximal holes 360.

Figure 16:
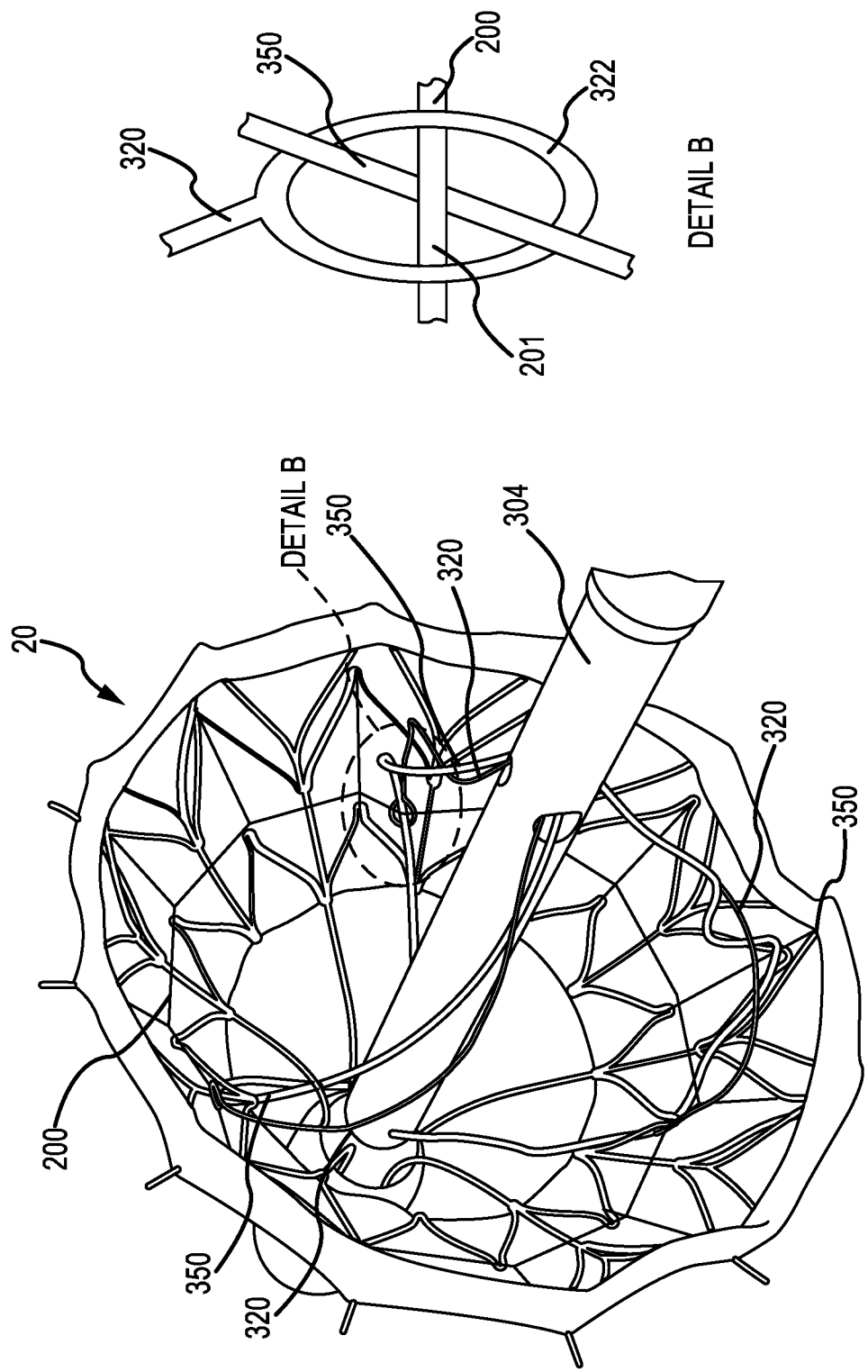
FIG. 16 is an illustration of a distal perspective view of the implant coupled to the delivery tool and in an expanded state.
Figure 17:
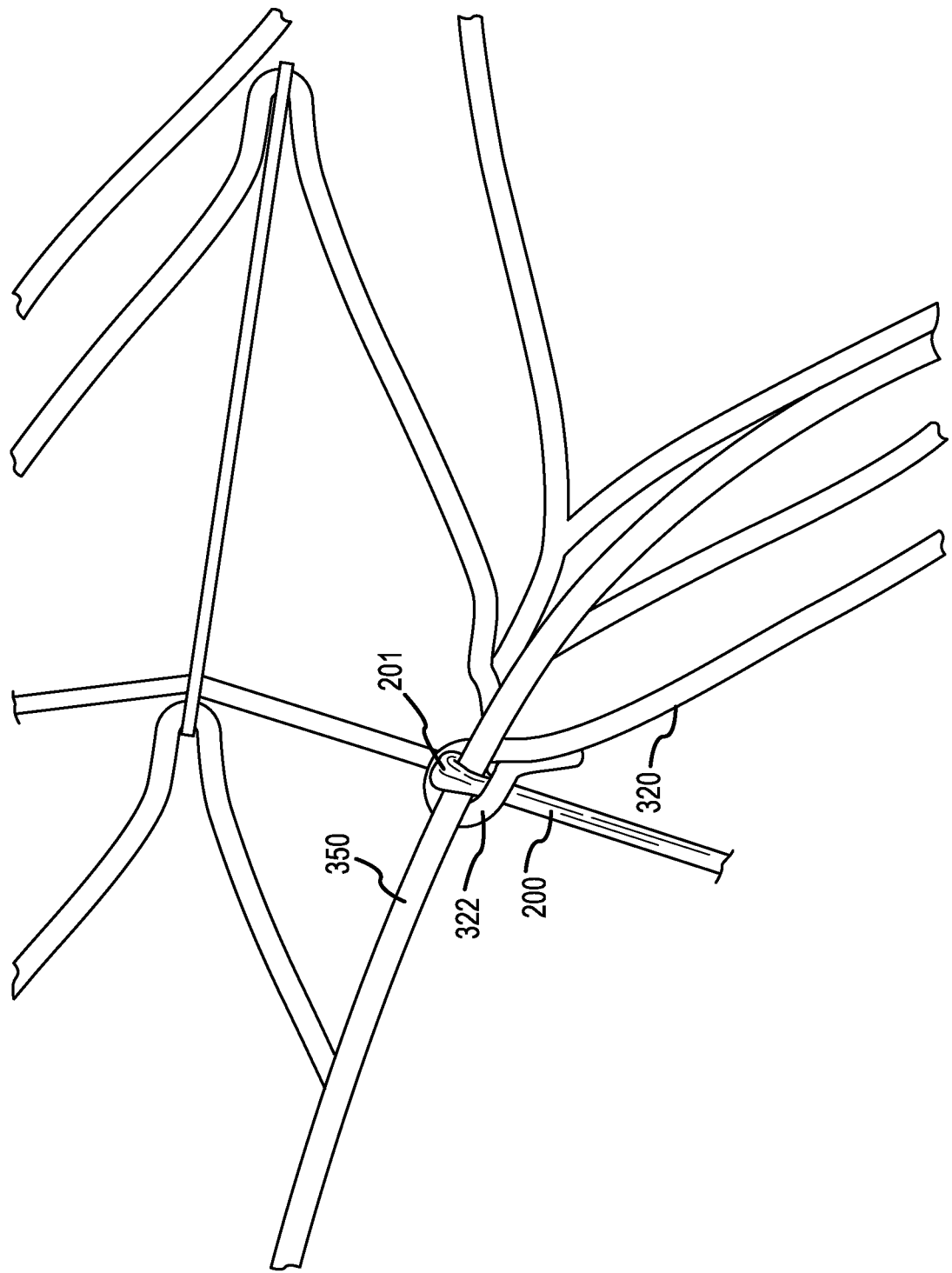
FIG. 17 is an illustration of a detailed view of a connection between the delivery tool and the tension control line of the implant and, more specifically connection between a tension control member of the delivery tool and the control line of the implant using a release line of the delivery tool.
Figure 18:
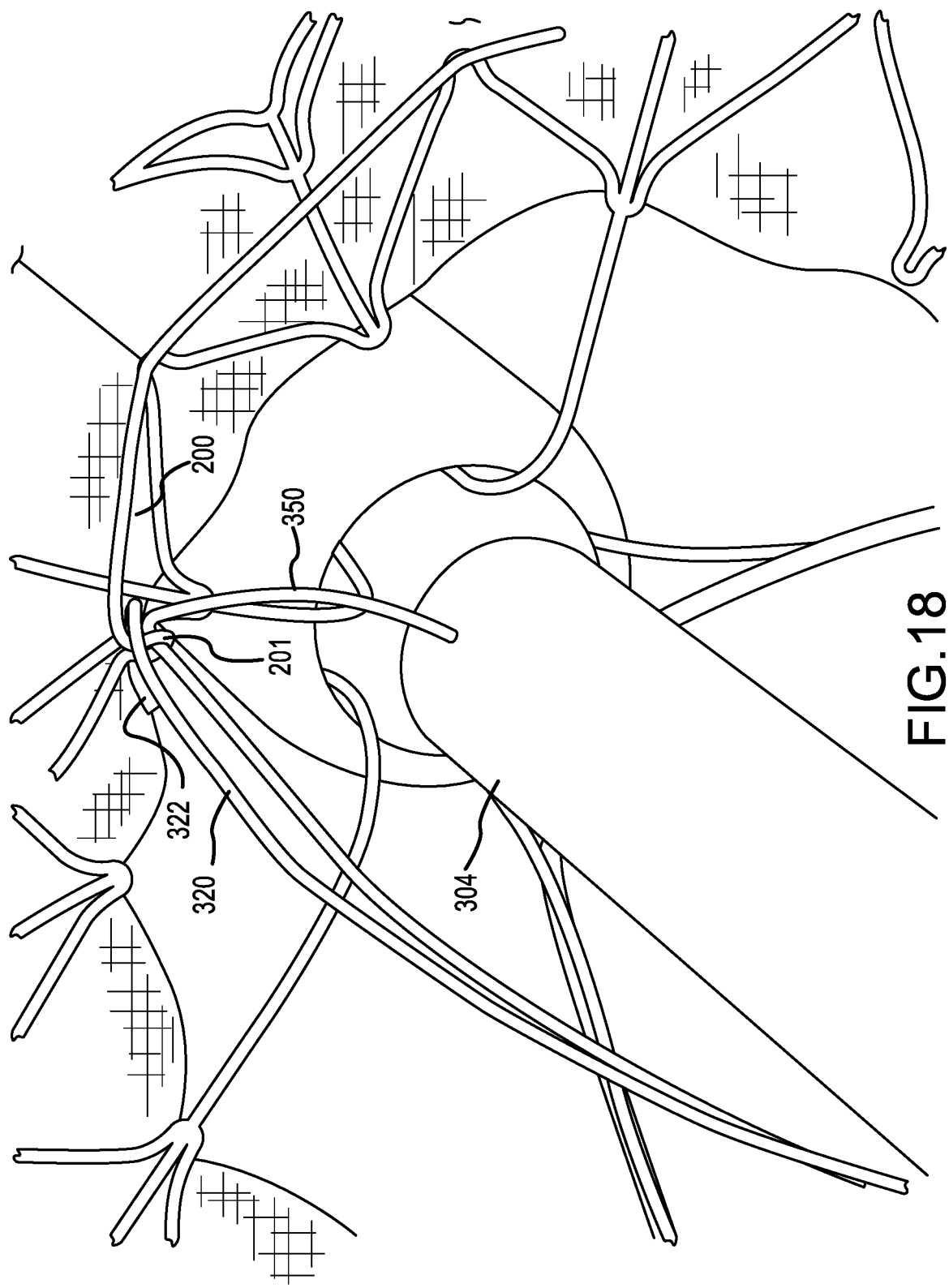
FIG. 18 is an illustration of a second detailed view of a connection between the delivery tool and the tension control line of the implant.

The implant 20 is generally coupled to the delivery tool 300 by coupling the implant 20 to the tension control members 320 using the release lines 350. FIG. 16 is an illustration of a proximal perspective view of the implant 20 coupled to the delivery tool 300 in an expanded state to illustrate such coupling. As illustrated in Detail B of FIG. 16, a loop 201 of the tension control line 200 is pulled through the loop 322 of the tension control member 320. The release line 350 is then passed through the loop 201 of the tension control line 200 and across the loop 322 of the tension control member 320, thereby retaining the loop 201 of the tension control line 200 through the loop 322 of the tension control member 320. To release the coupling between the control line 200 and the tension control member 320, the release line 350 is slid out of the loop 201, thereby enabling the loop 201 to pass through the loop 322 of the tension control member 320 and decoupling the tension control member 320 from the control line 200. Detailed illustrations of the loop 201 of the tension control line 200 coupled to the loop 322 of the tension control member 320 are provided in FIGS. 17 and 18.

Referring back to FIG. 15, routing of the release lines 350 generally includes routing the release lines 350 (shown in dashed lines for clarity and distinction over other illustrated elements) through the catheter body 352 to an exterior thereof, such as by passing the release lines 350 through the distal holes 362 of the catheter body 352. The release lines 350 may then be routed proximally to join the control line 200 to the tension control members 320, as noted above and as illustrated in FIGS. 16-18. The release lines 350 may then be routed proximally and back into the catheter body 352 through the proximal holes 360 where the release lines 350 may be retained, e.g., by friction, until the implant 20 is to be released.

As shown in FIG. 15, in at least certain implementations, the occluder 50 of the implant 20 may include a proximally extending annular protrusion 51 defining each of a proximally open annulus 53 and laterally extending holes 57 in communication with the annulus 53. In such implementations, the annular protrusion 51 may be disposed within the distal opening 357 (shown in FIG. 14) of the release catheter 304 during insertion and delivery to an implantation location and the release lines 350 may be further routed into the annulus 53 and through the holes 57 before being passed through the distal holes 362 of the catheter body 352.

Figure 20:
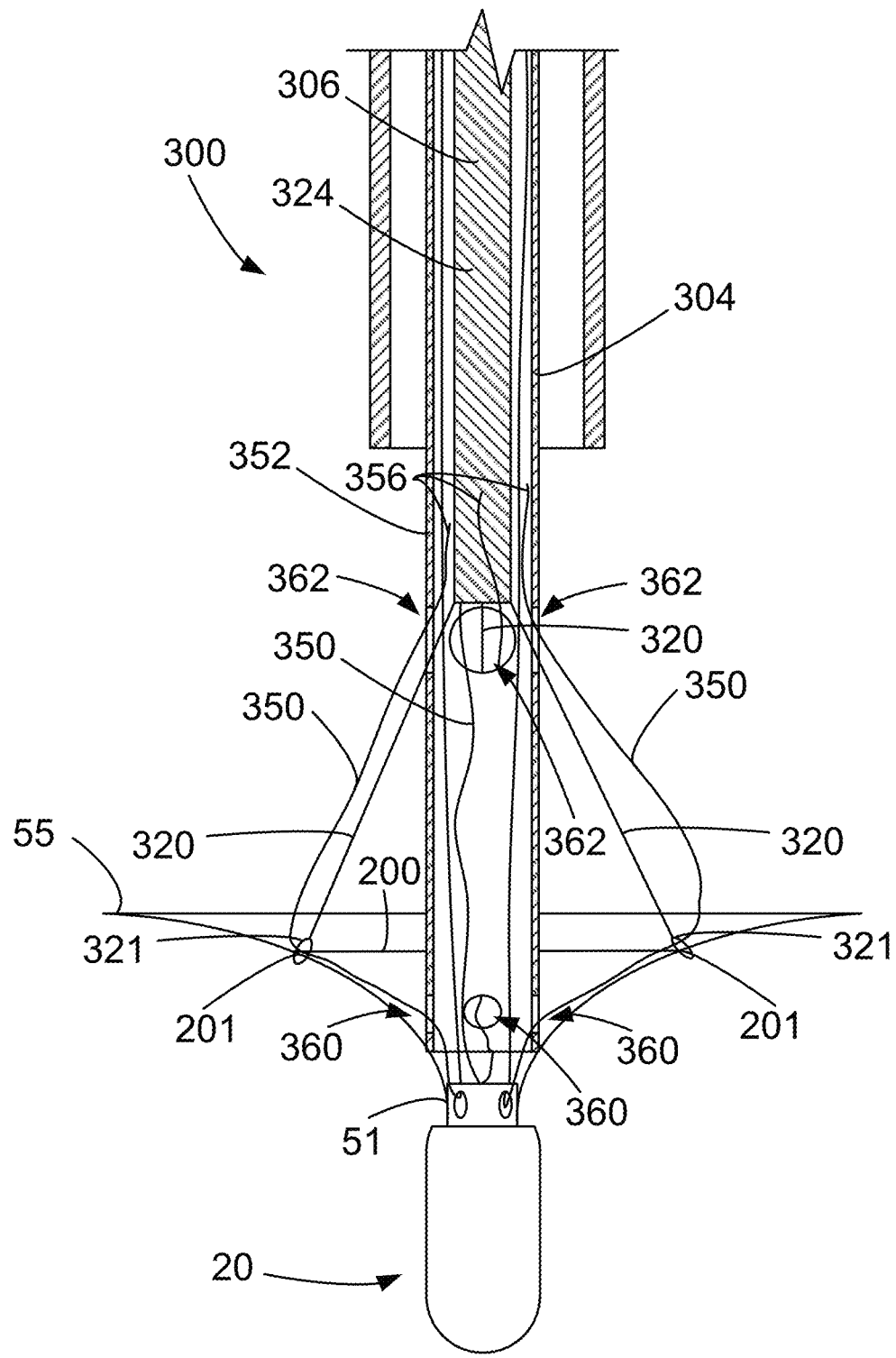
FIG. 20 is a side cross-sectional view of the delivery tool coupled to the implant with the implant in an expanded configuration.
Figure 21:
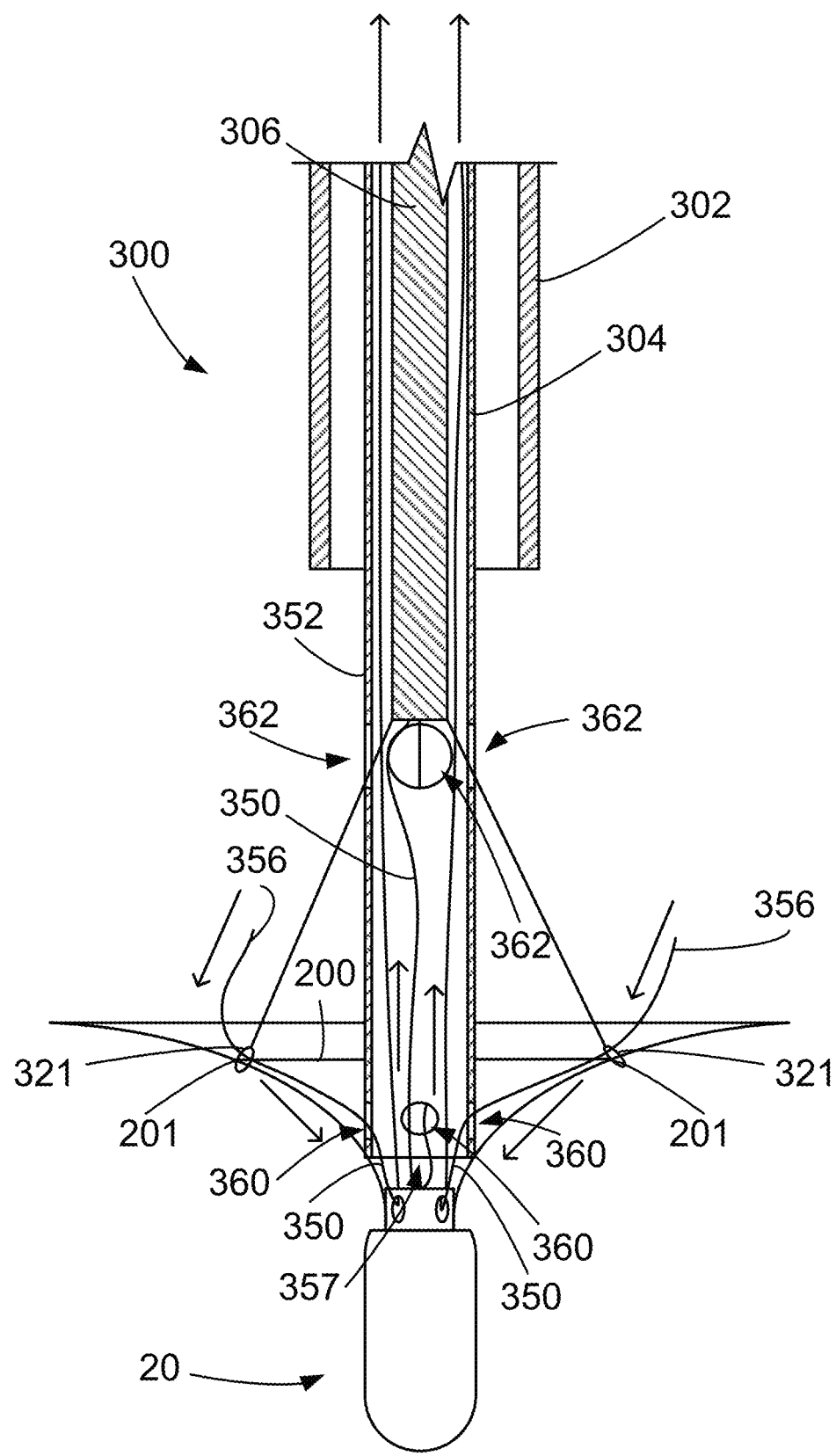
FIG. 21 is a side cross-sectional view of the delivery tool and the implant during release of the implant from the delivery tool.
Figure 22:
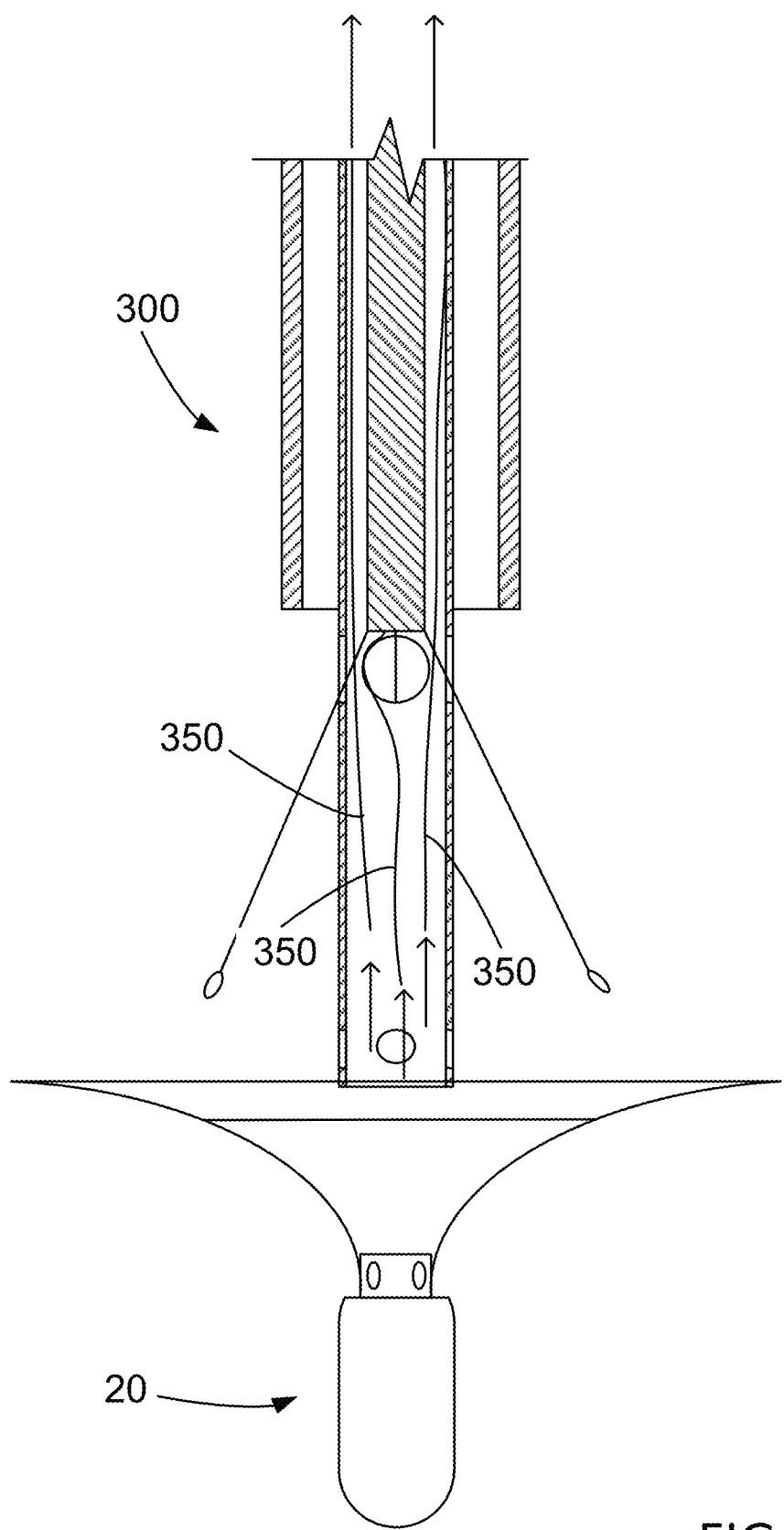
FIG. 22 is a side cross-sectional view of the delivery tool and the implant following release of the implant from the delivery tool.

FIGS. 20-22 illustrate the general process of releasing the implant 20 from the delivery tool 300. Referring first to FIG. 20, the delivery tool 300 and implant 20 are shown with the frame 55 of the implant 20 in an expanded configuration but still coupled to the delivery tool 300. More specifically, the implant 20 is coupled to the delivery tool 300 by virtue of the release lines 350 of the release catheter 304, each of which is routed, in order, through the catheter body 352, through the annular protrusion 51 of the implant 20, through one of the distal holes 362 of the catheter body 352, through one of the loops 201 of the tension control line 200 extending through a loop 321 of one of the tension control members 320, and back into the catheter body 352 through one of the proximal holes 360. As previously noted, in at least certain implementations, the ends 356 of the release lines 350 may be retained within the catheter body 352 by friction.

In the state illustrated in FIG. 20, the tension control shaft 324 of the tension control assembly 306 may be actuated (e.g., by translating and/or rotating the shaft or a handle assembly coupled to the shaft) to vary the tension applied to the frame 55 of the implant 20. By doing so, the frame 55 may be expanded and/or collapsed to facilitate placement of the implant 20 prior to release of the implant 20 from the delivery tool 300.

Referring next to FIG. 21, the delivery tool 300 and implant 20 are illustrated part way through release of the implant 20 from the delivery tool 300. In general, release of the implant 20 from the delivery tool 300 is performed by pulling the release lines 350 proximally through the catheter body 352. As illustrated and for each release line 350 and as indicated by the open arrows, such pulling causes the end 356 of the release line 350 to exit the catheter body 352 through one of the proximal holes 360, pass through one of the loops 201 of the tension control line 200 to release the loop 201 from a corresponding control member 320, pass through one of the distal holes 362 of the catheter body 352 and the annular protrusion 51 of the implant 20, and reenter the catheter body 352 through the distal opening 357 of the catheter body 352. As a result, pulling the release lines 350 decouples the implant from the delivery tool and allows removal of the delivery tool 300 with the implant 20 remaining in place, as shown in FIG. 22. Following release of the implant 20, each of the release catheter 304 and the tension control assembly 306 may be proximally retracted and/or proximally removed from the sheath 302.

Notably, the process of releasing the implant 20 from the delivery tool 300 by pulling the release lines 350 applies a net force on the implant 20 that expands the frame 55 and/or resists collapse of the frame 55. More specifically, as the release lines 350 are pulled to release the implant 20, the release lines 350 apply a net distal force on the implant 20, thereby pressing the implant 20 into its current implantation location. Moreover, because such distal force is applied at the connection between the control line 200 and the tension control member 320 it acts to further expand or otherwise provide additional counterforce against collapse of the frame 55. In contrast, if a net proximal force were to be applied, the implant 20 may be pulled out of place and/or the frame 55 may undergo a partial collapse, each potentially leading to the implant 20 becoming dislodged or losing its orientation. Accordingly, by routing the release lines 350 as noted above, proper placement of the implant 20 is more easily controlled and more likely to be maintained following release of the implant 20.

VI. Multi-Part Occluder

Figure 23:
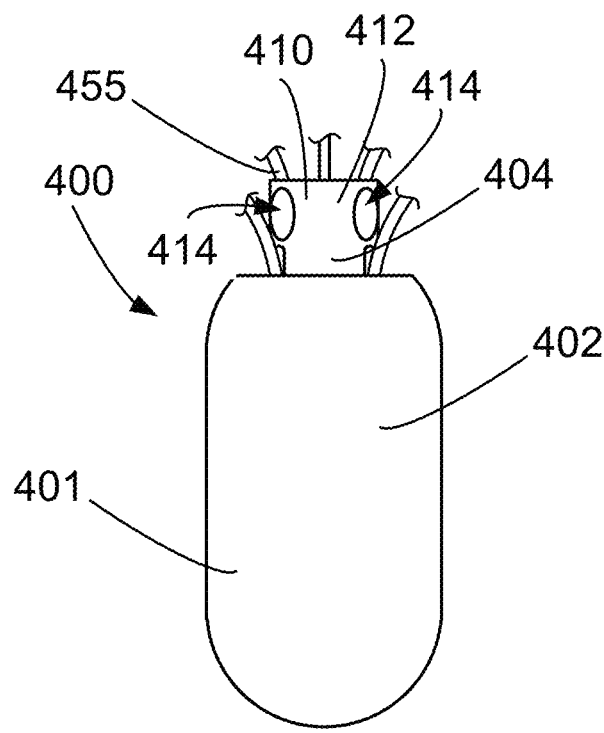
FIG. 23 is a side elevation view of a distal portion of an implant.
Figure 24:
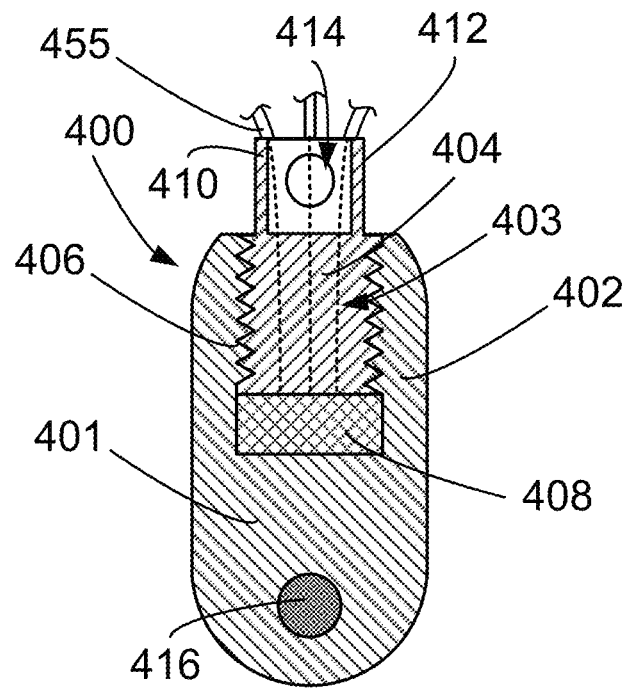
FIG. 24 is a side cross-sectional view of the distal portion of the implant of FIG. 23.

FIGS. 23 and 24 illustrate a distal portion of an example implant 400 that may be used in implementations of the present disclosure. More specifically, FIG. 23 is a side elevation view of the distal portion of the implant 400 while FIG. 24 is a cross-sectional view of the implant 400, each of which emphasize an occluder 401 of the implant 400.

As illustrated, the occluder 401 includes an occluder body 402 defining a cavity 403 within which an insert 404 is disposed. The insert 404 is coupled to the occluder body 402. In the specific implementation illustrated in FIGS. 23 and 24, the insert 404 is coupled to the occluder body 402 by a threaded connection 406; however, any suitable connection (e.g., adhesive, welding, etc.) may be used instead of a threaded connection.

The occluder 401 further includes a frame base 408 disposed within the cavity 403 of the occluder body 402 and distal the insert 404. The frame base 408 is coupled to a frame 455 of the implant 400 (shown in part and which may be substantially similar to other frames disclosed herein) which extends from the frame base 408 and exits proximally from the occluder body 402. The frame base 408 may be coupled to the occluder body 402 and/or may be maintained in place by the insert 404.

The insert 404 further includes a proximally extending annular protrusion 410. The annular protrusion 410 includes a sidewall 412 through which one or more laterally extending holes 414 may be defined. As previously discussed in the context of FIGS. 15 and 20-22, during use of systems disclosed herein, release lines of a delivery tool may be routed through the holes 414 to secure the implant 400 to a delivery tool and, more specifically, to a release catheter of a delivery tool.

The occluder 401 further includes a marker 416 disposed within the occluder body 402. In certain implementations, the marker 416 may be a radiopaque marker to facilitate fluoroscopic observation of the implant 400 during delivery and implantation. As shown, the marker 416 may be embedded within the occluder body 402, such as by molding the occluder body 402 about the marker 416. In other implementations, the cavity 403 may be shaped to receive the marker 416 in addition to the insert 404 and the frame base 408. In still other implementations, the marker 416 may be disposed on an exterior surface of the occluder body 402. Although illustrated as a spherical bead in FIG. 24, the marker 416 may be have any suitable shape. Similarly, any suitable number of markers may be incorporated into the occluder body 402. In other implementations, the occluder body 402 may be formed from a material with radiopaque additives. In still other implementations, either or both of the frame base 408 and the insert 404 may be formed of radiopaque material or include one or more radiopaque markers.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A cardiac valve repair implant comprising:
a central occluder including a central longitudinal axis;
a frame extending proximally from the central occluder, the frame centered about and forming a circumference around the central longitudinal axis of the central occluder, the frame self-biasing from a collapsed state to an expanded state, wherein a proximal end of the frame projects proximally when the frame is in the collapsed state, and wherein the proximal end of the frame projects radially outward away from the central longitudinal axis of the central occluder when the frame is in the expanded state; and
a thin sheet supported on a proximal portion of the frame, wherein when the frame is in the expanded state, the thin sheet forms an annular surface defining an inner circular opening centered about the central longitudinal axis of the central occluder;
wherein the frame includes spokes that extend between a proximal end of the central occluder and the proximal portion of the frame that supports the thin sheet, and
wherein the proximal portion of the frame that supports the thin sheet includes arcuate petal portions extending from the spokes.

2. The cardiac valve repair implant of claim 1, wherein the frame includes anchor members on a distal side of the frame, the anchor members protruding distally from the frame when the frame is in the expanded state.

3. The cardiac valve repair implant of claim 2, wherein the anchor members additionally protrude radially outward when the frame is in the expanded state.

4. The cardiac valve repair implant of claim 2, wherein the anchor members additionally protrude radially inward when the frame is in the expanded state.

5. The cardiac valve repair implant of claim 1, wherein the spokes are substantially straight and substantially parallel to the central longitudinal axis of the central occluder when the frame is in the collapsed state, and the spokes curve radially outward relative to the central longitudinal axis of the central occluder when the frame is in the expanded state.

6. The cardiac valve repair implant of claim 1, wherein each arcuate petal portion includes an outer arcuate member and an inner arcuate member radially inward of the outer arcuate member.

7. The cardiac valve repair implant of claim 1, wherein the thin sheet is supported on a distal side of the frame.

8. The cardiac valve repair implant of claim 1, wherein the thin sheet is supported on a proximal side of the frame.

9. The cardiac valve repair implant of claim 1, wherein the central occluder includes a cylindrical side surface and a bullnose extending distally from the cylindrical side surface.

10. The cardiac valve repair implant of claim 1, wherein the frame includes a shape-memory material that self-biases the frame from the collapsed state to the expanded state.

11. The cardiac valve repair implant of claim 1, wherein the thin sheet includes a fabric material that allows for tissue ingrowth.

12. A method of repairing target cardiac valves, the method comprising:
delivering an implant in a collapsed state into an atrium adjacent a target cardiac valve, the implant including a central occluder with a central longitudinal axis, a frame extending proximally from the central occluder, and a thin sheet supported on a proximal region of the frame, wherein when the implant is in the collapsed state, the frame and thin sheet are folded inward about the central longitudinal axis;
approaching the target cardiac valve with the implant in an expanded state, wherein when the implant is in the expanded state, the frame and thin sheet are unfolded and form an annular structure defining an inner circular opening centered about the central longitudinal axis of the central occluder; and
positioning the central occluder in an orifice of the target cardiac valve and a distal side of the annular structure against an annular region of cardiac tissue surrounding the target cardiac valve such that the inner circular opening opens over the orifice of the target cardiac valve,
wherein the frame includes spokes that extend between a proximal end of the central occluder and the proximal region of the frame that supports the thin sheet, and
wherein the proximal region of the frame that supports the thin sheet includes arcuate petal portions extending from the spokes.

13. The method of claim 12, wherein the implant is delivered to the target valve via an antegrade percutaneous route.

14. The method of claim 12, wherein the implant self-biases from the collapsed state to the expanded state.

15. The method of claim 12, wherein a proximal end of the frame projects proximally when the frame is in the collapsed state, and wherein the proximal end of the frame projects radially outward away from the central longitudinal axis of the occluder when the frame is in the expanded state.

16. The method of claim 12, wherein the frame includes anchor members on a distal side of the annular structure, and the anchor members protrude into the annular region of cardiac tissue surrounding the target cardiac valve.

17. The method of claim 16, further comprising over expanding the implant to cause the anchor members to protrude into the annular region.

18. The method of claim 16, further comprising pushing the implant distally against the annular region of cardiac tissue surrounding the target cardiac valve to cause the anchor members to protrude into the annular region.

19. The method of claim 12, wherein the frame includes a shape-memory material that self-biases the implant from the collapsed state to the expanded state.

20. The method of claim 12, wherein the thin sheet includes a fabric material that allows for tissue ingrowth.

21. The method of claim 12, wherein the central occluder is positioned in the orifice of the target cardiac valve such that leaflets of the target cardiac valve abut against a cylindrical side of the central occluder.

* * * * *